US008317738B2

(12) United States Patent
Ishida et al.

(10) Patent No.: US 8,317,738 B2
(45) Date of Patent: *Nov. 27, 2012

(54) LIQUID COLLECTION CONTAINER AND EXTRACORPOREAL CIRCUIT

(75) Inventors: Norikazu Ishida, Fujinomiya (JP); Hidetaka Nakayama, Fujinomiya (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 724 days.

This patent is subject to a terminal disclaimer.

(21) Appl. No.: 12/355,428

(22) Filed: Jan. 16, 2009

(65) Prior Publication Data

US 2009/0187132 A1   Jul. 23, 2009

(30) Foreign Application Priority Data

Jan. 22, 2008  (JP) ................................ 2008-011982

(51) Int. Cl.
*A61M 37/00* (2006.01)
*A61M 1/00* (2006.01)
*A61M 31/00* (2006.01)

(52) U.S. Cl. .......... 604/6.11; 604/6.14; 604/27; 604/48; 604/500; 604/93.01; 422/45

(58) Field of Classification Search .................. 604/6.14, 604/27, 48, 500, 93.01; 422/45
See application file for complete search history.

(56) References Cited

U.S. PATENT DOCUMENTS

| | | | | |
|---|---|---|---|---|
| 3,655,123 | A | * | 4/1972 | Judson et al. ................... 422/44 |
| 3,890,969 | A | * | 6/1975 | Fischel ......................... 604/6.14 |
| 3,985,135 | A | * | 10/1976 | Carpenter et al. ............. 604/410 |
| 4,605,503 | A | * | 8/1986 | Bilstad et al. ................. 210/651 |
| 4,765,959 | A | * | 8/1988 | Fukasawa ....................... 422/48 |
| 5,282,783 | A | | 2/1994 | Lindsay |
| 6,908,446 | B2 | | 6/2005 | Yokoyama et al. |
| 2002/0009386 | A1 | * | 1/2002 | Lindsay .......................... 422/45 |
| 2006/0089586 | A1 | * | 4/2006 | Kaus et al. .................... 604/4.01 |
| 2007/0100273 | A1 | * | 5/2007 | Kawarabata et al. ......... 604/6.15 |
| 2007/0258856 | A1 | * | 11/2007 | Olsen et al. ..................... 422/45 |
| 2008/0262405 | A1 | | 10/2008 | Ogihara et al. |

FOREIGN PATENT DOCUMENTS

WO   WO 2006/047147 A1   5/2006

OTHER PUBLICATIONS

Extended European Search Report issued in corresponding EP 08 15 4464.5, Jul. 18, 2008, EPO, Munich, DE.

(Continued)

*Primary Examiner* — Leslie Deak
*Assistant Examiner* — Adam Marcetich
(74) *Attorney, Agent, or Firm* — Buchanan Ingersoll & Rooney PC

(57) ABSTRACT

A liquid collection bag is used as a part of an extracorporeal circuit and is connected via a tube to a storage container containing a priming solution. The collection container collects the priming solution from the storage container by a pressure differential between the pressure inside the collection container and the pressure inside the storage container. The liquid collection container is a flexible bag body having a partition part dividing the inside of the bag body into a first space and a second space. In addition, a communication part communicates the first space with the second space.

20 Claims, 19 Drawing Sheets

OTHER PUBLICATIONS

Rosengart, MD, Todd K., et al., "Retrograde Autologous Priming for Cardiopulmonary Bypass: A Safe and Effective Means of Decreasing Hemodilution and Transfusion Requirements," *The Journal of Thoracic and Cardiovascular Surgery*, Feb. 1, 1998, pp. 426-439, vol. 115, No. 2, Mosby-Year Book, Inc., St. Louis, MO, USA.

Eising, M.D., Gregory, P., et al,, "Retrograde Autologous Priming: Is It Useful in Elective On-Pump Coronary Artery Bypass Surgery?", *Ann. Thorac. Surg.*, Jan. 2003, pp. 23-27, vol. 75, Issue 1,The Society of Thoracic Surgeons, Elsevier Science Inc.

Balachandran, FRCA, Subramaniam, et al., "Retrograde Autologous Priming of the Cardipulmonary Bypass Circuit Reduces Blood Transfusion After Coronary Artery Surgery," *Ann. Thorac. Surg.*, Jun. 2002, pp. 1912-1918, vol. 73, Issue 6, The Society of Thoracic Surgeons, Elsevier Science Inc.

Cormack, CCP, John E., et al,, "Hematocrit Prediction and Preservation for Cardiopulmonary Bypass," *E-Journal of Perfusion Technology*, Jun. 16, 2003, http://perfline.com/ejournal/2002/jec0102.html.

\* cited by examiner

LIQUID COLLECTION CONTAINER AND EXTRACORPOREAL CIRCUIT

TECHNOLOGICAL FIELD

The present invention relates to a liquid collection container and an extracorporeal circuit.

BACKGROUND DISCUSSION

U.S. Pat. No. 6,908,446 describes an extracorporeal circuit (extracorporeal apparatus) which extracorporeally circulates blood. The extracorporeal circuit includes a venous line and an arterial line which are connected to a patient, a blood reservoir connected on a downstream side of the venous line, an oxygenator connected on an upstream side of the arterial line, and a linkage line which links the blood reservoir and the oxygenator.

When the extracorporeal circuit (hereinafter, simply, circuit) described in the aforementioned patent is used to extracorporeally circulate blood, a priming solution (for example, physiological saline) is first fed into the circuit to prime the circuit. Thereafter, extracorporeal circulation is performed. When such an operation is performed, blood is diluted with the priming solution (hemodilution).

In recent years, a technique of collecting the priming solution as much as possible so as to hinder blood dilution (hemodilution), i.e., an increase in dilution ratio of blood, has been adopted prior to performing extracorporeal circulation. The technique is generally referred to as retrograde autologous priming (RAP). To carry out RAP, a collection bag for collecting the priming solution is connected to the circuit in advance. In this state, blood is drawn from a patient to the circuit in a direction opposite to the direction of the normal flow of blood during extracorporeal circulation. Thus, the priming solution in the circuit is thrust toward the collection bag by the blood. As a result, the priming solution is collected into the collection bag.

As the collection bag, the one formed by fusing the edges of two sheet materials having flexibility is usable. In the collection bag, the respective parts not fused to each other of the two sheet materials (the parts other than the fused part) define the storage space in which a priming solution is stored. Herein, the part of each sheet material defining the storage space is referred to as a "storage space defining part". The collection bag is configured such that the storage space defining parts are in close contact with each other in such a state that a priming solution has not yet been stored in the storage space, i.e., in an unused state. When the priming solution starts to flow into the storage space from this state, the storage space defining parts are separated away from each other, resulting in an increase in volume of the storage space. Therefore, the pressure in the storage space decreases. At this time, the priming solution is excessively (involuntarily) drawn into (flows into) the storage space from the circuit. Then, the priming solution further flows into the storage space, and the volume of the priming solution in the storage space approaches the maximum volume. The pressure in the storage space increases to such a degree as to thrust the priming solution back to the circuit side, i.e., to hinder the flow of the priming solution into the storage space. At this point, it becomes impossible to collect the priming solution. Thus, the priming solution cannot be collected in the proper quantity when the priming solution is desired to be collected.

SUMMARY

An extracorporeal circuit for extracorporeally circulating blood comprises a blood reservoir, an arterial line connectable to a patient during extracorporeal circulation to receive blood from the patient, and a venous line connectable to a patient during extracorporeal circulation to return blood to the patient. The blood reservoir possesses a storage chamber for temporarily storing liquid, and a tube having an upper end. A pump is connected to the lower end opening of the blood reservoir, and the upper end of the tube of the blood reservoir is connectable to a source of priming solution. An oxygenator is connected to the arterial line and the pump to effect gas exchange on the blood from the patient, and a flexible collection container possesses an interior for collecting the priming solution. A partition in the interior of the collection container divides the interior of the collection container into a first space positioned above a second space. A branch line is in fluid communication with the venous line and branches from the venous line, and the first space is in fluid communication with the branch line. The interior of the collection container comprises a communication part for establishing communication between the first space and the second space. The priming solution is introduced into the first space by way of the branch line, and is collected in the second space via the communication part.

Another aspect of the disclosure here involves a liquid collection bag in combination with a storage container. The liquid collection bag possesses an interior connected in a fluid communicating manner to the interior of the storage container by way of a tube, with the interior of the liquid collection bag being adapted to receive and collect liquid from the storage container based on a difference in pressure between an inside of the liquid collection bag and an inside of the storage container. The liquid collection bag comprises a flexible bag body enclosing the interior of the collection bag, with a partition part dividing the interior of the collection bag into a first space and a second space, and an introduction part connected to the tube and having an end positioned in the first space to introduce the liquid from the storage container which has passed through the tube into the first space. The bag body is provided with a communication part extending between the first and second spaces for establishing communication between the first space and the second space. The liquid from the storage container is introduced into the first space by way of the introduction part, and is collected into the second space by way of the communication part.

According to another aspect, a method of priming a circuit to be used in extracorporeal blood circulation comprises connecting a blood reservoir to a source of priming solution, wherein the circuit is comprised of an oxygenator, an arterial line connected to the oxygenator, a pump connected, a first line connecting in a fluid communicating manner the pump and the bottom of the blood reservoir, a second line connecting in a fluid communicating manner the pump and the oxygenator, a venous line connected to the blood reservoir, a flexible collection container possessing an interior, and a third line branching from the venous line and having an open end opening into the interior of the collection container. The method also comprises positioning the collection container so that the open end of the third line is positioned elevationally below an objective height in the blood reservoir, and introducing the priming solution into the blood reservoir from the source while the third line is closed, wherein the priming solution flows from the blood reservoir through the first line, through the pump, through the second line, through the oxygenator and through the arterial line. In addition, the third line is opened after the priming solution in the blood reservoir is elevationally at or above the objective height so that the priming solution automatically flows into the collection container.

DETAILED DESCRIPTION

Figure 1:
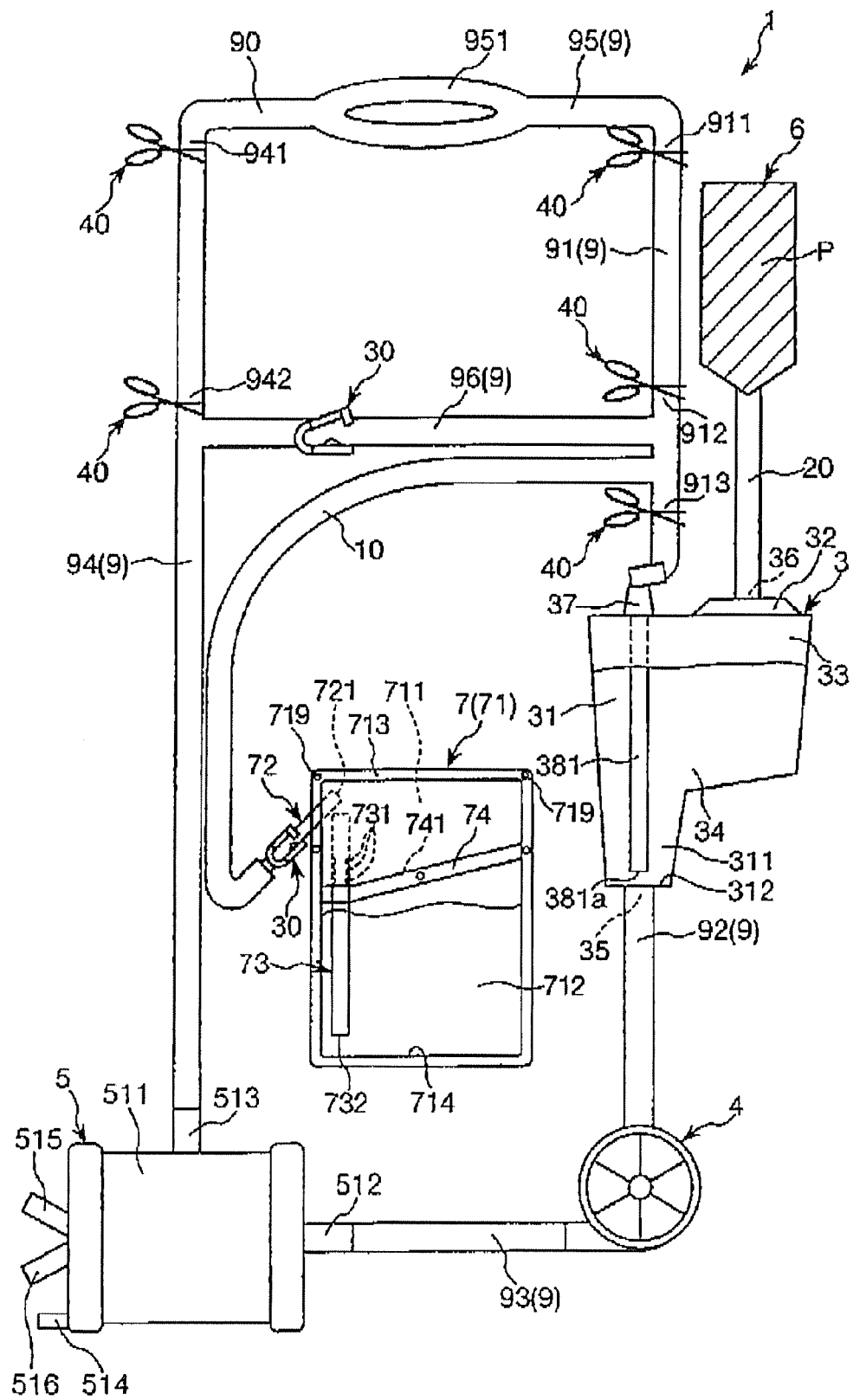
FIG. 1 is a schematic illustration of an example of the circuitry of an extracorporeal circuit showing one aspect of the manner of use of the extracorporeal circuit disclosed here.
Figure 11:
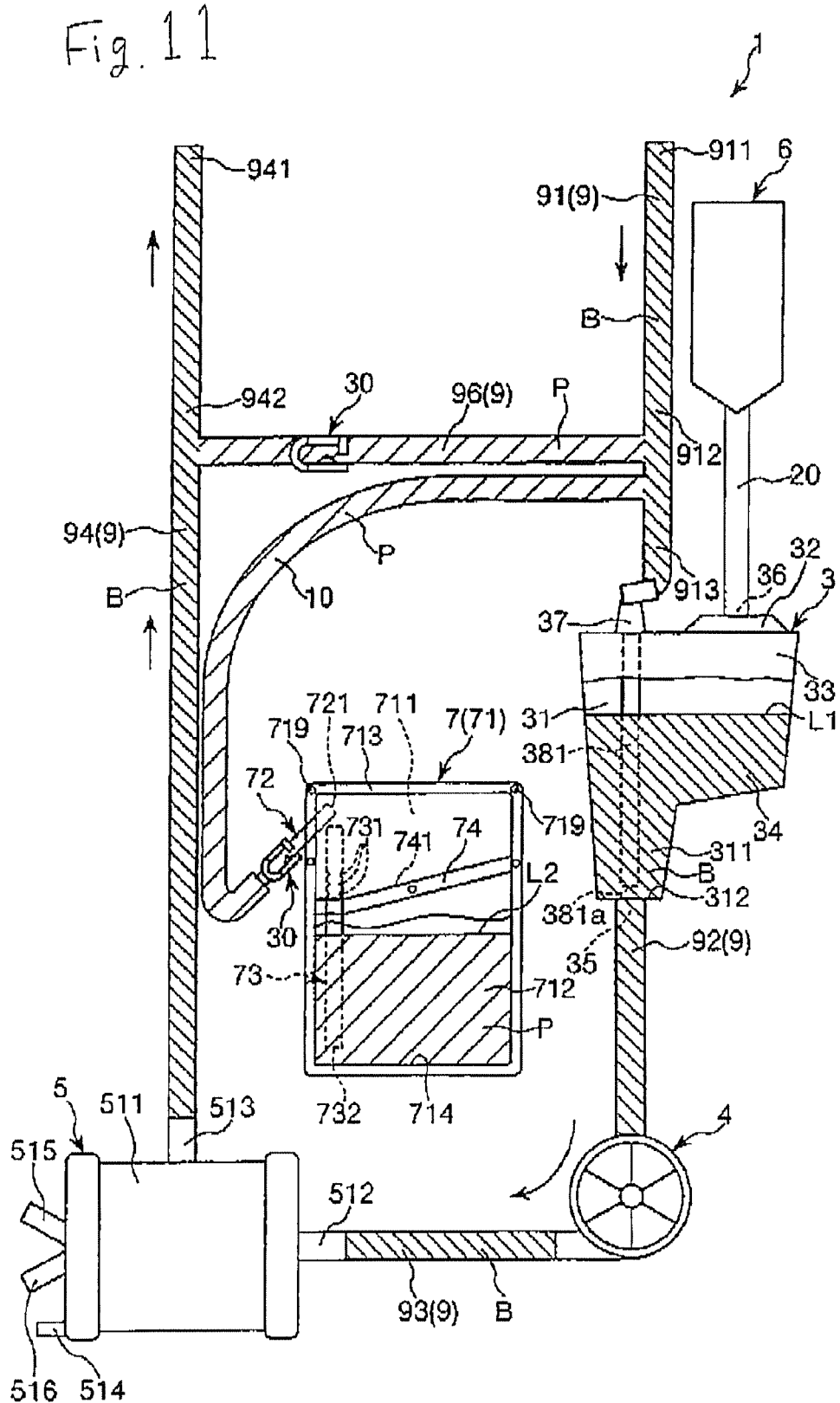
FIG. 11 is a schematic illustration of the circuitry of the extracorporeal circuit illustrated in FIG. 1 showing a further aspect of the manner of use of the disclosed extracorporeal circuit.
Figure 12:
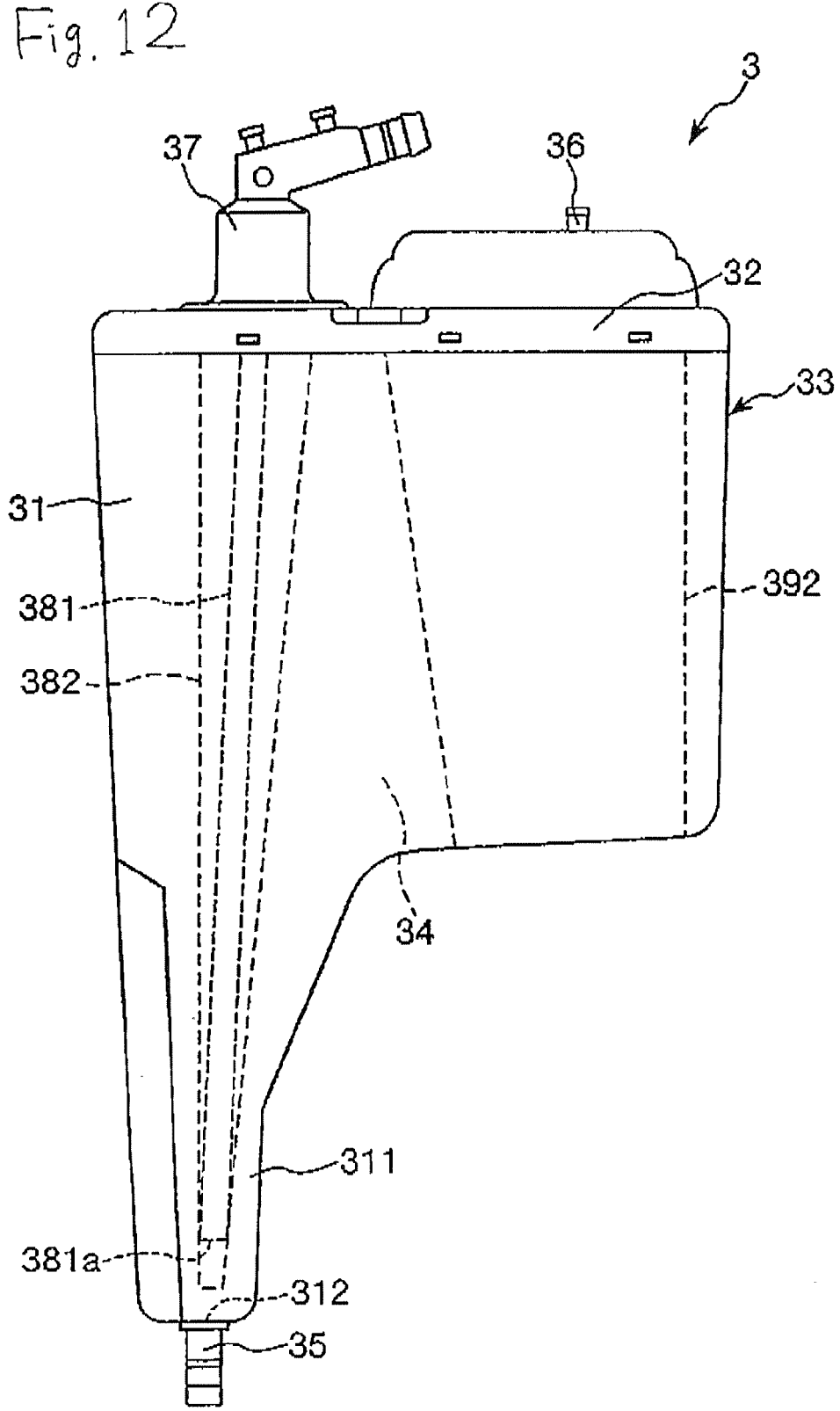
FIG. 12 is a side view of a blood reservoir included in the extracorporeal circuit shown in FIG. 1.
Figure 13:
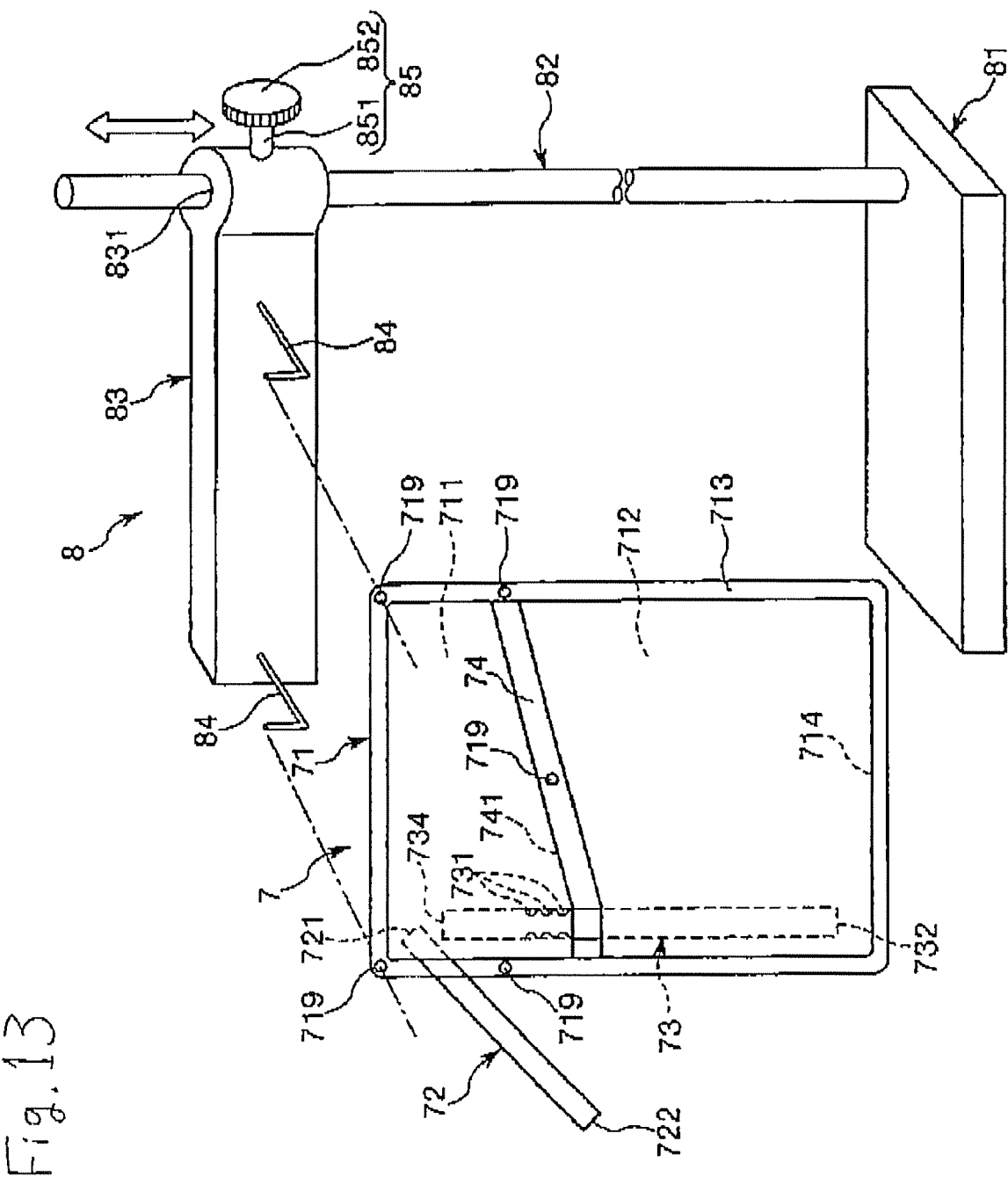
FIG. 13 is a perspective view of a liquid collection container or bag in the use condition and included in the extracorporeal circuit shown in FIG. 1.
Figure 14:
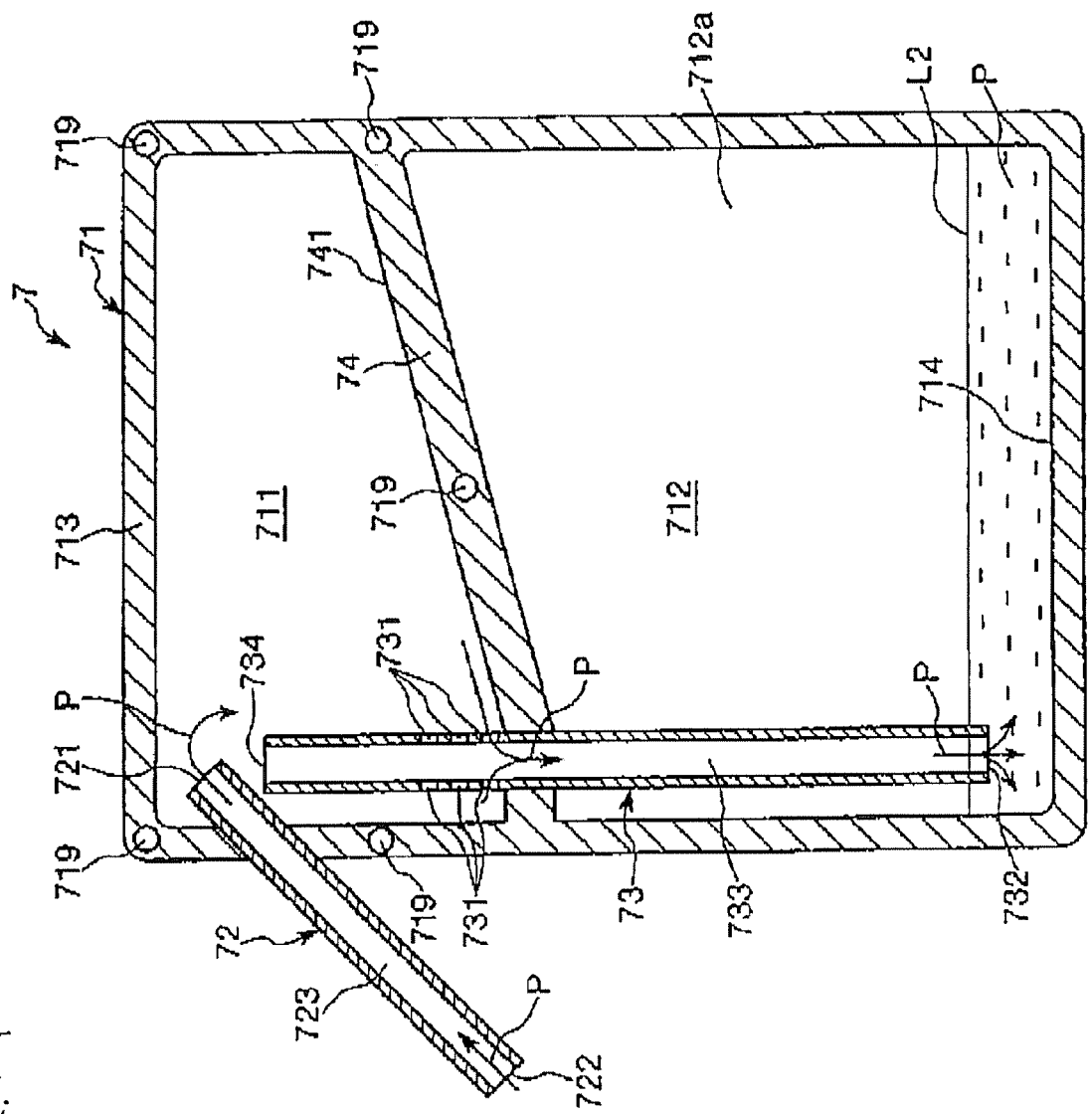
FIG. 14 is a longitudinal cross-sectional view of the liquid collection bag shown in FIG. 13.

FIGS. 1-11 illustrate an example of the circuitry of an extracorporeal circuit according to one embodiment disclosed here. FIG. 12 is a side view of the blood reservoir included in the FIG. 1 extracorporeal circuit, FIG. 13 is a perspective view showing a manner of use of one embodiment of the liquid collection bag included in the extracorporeal circuit shown in FIG. 1, and FIG. 14 is a longitudinal cross-sectional view of the liquid collection bag shown in FIG. 13.

In the description below, for the sake of convenience, the upper part of FIGS. 12-14 (as well as FIGS. 15-2 discussed below) are referred to as the "top" or "upper part", while the lower part thereof is referred to as the "bottom" or "lower part".

The extracorporeal circuit 1 shown in FIGS. 1-11 extracorporeally circulates blood B. The extracorporeal circuit 1 is a circuit capable of performing RAP (Retrograde Autologous Priming). The term "RAP" as used here refers to a technique for hindering dilution of blood with the priming solution P (hemodilution) by collecting the priming solution P as much as possible before normal extracorporeal circulation of blood B (for simplicity, the extracorporeal circulation of blood B is referred to as extracorporeal circulation) is performed (see FIG. 11) after the extracorporeal circuit 1 is primed (filled with the priming solution P).

As shown in FIG. 1, the extracorporeal circuit 1 includes a circuit body 9 composed of four substantially transparent tubes 90, 92, 93, 96, a blood reservoir 3 connected to the tubes, a pump (centrifugal pump) 4, and an oxygenator 5. Moreover, the extracorporeal circuit 1 includes, in addition to these components, a bag 6 storing a priming solution P, a substantially transparent tube 20 fluidly communicating the bag 6 and the blood reservoir 3, a substantially transparent tube (branch line) 10 branching out from the circuit body 9 (tube 91), and a liquid collection bag (simply hereinafter referred to as a (collection bag)) 7 connected to the tube 10, a stand or support 8 (collection bag support device) for supporting the collection bag 7, and two clamps 30 for opening and closing the tubes 96 and 10, respectively.

In this embodiment, for convenience of description, the portion of the tube 90 extending in a vertical direction on the blood reservoir 3 side (right side) in FIG. 1 is referred to as the "tube 91", the portion of the tube 90 extending in the vertical direction on the oxygenator 5 side (left side) in FIG. 1 is referred to as the "tube 94", and the portion of the tube 90 extending in the lateral direction between the tube 91 and the tube 94 is referred to as the "tube 95".

The blood reservoir 3 shown in FIG. 12 temporarily stores a liquid (e.g., blood B or a priming solution P) in the extracorporeal circuit 1. The blood reservoir 3 includes a housing 33 composed of a housing body 31 and a cover 32. A liquid storage space (storage chamber) 34 exists inside the housing 33 for storing a liquid (blood) is formed.

The housing body 31 is in the shape of a box having a downwardly projecting projection 311 at the lower left side as shown in FIG. 12. At the lower part of the projection 311, a tubular connecting port (opening) 35 communicating with the liquid storage space 34 is formed.

The cover 32 is engaged with the upper end of the housing body 31 to cover the upper opening of the housing body 31. At prescribed positions of the cover 32, tubular connecting ports (openings) 36, 37 are formed.

The connecting ports 35-37 are connected in the extracorporeal circuit 1 as follows. As shown in FIG. 11, the tube 91 is connected to the connecting port 37. The tube 91 functions as a venous line. As a result, for performing extracorporeal circulation, blood from a patient flows into the housing 33 via the connecting port 37.

The tube 20 is connected to the connecting port 36. The blood reservoir 3 and the feed bag 6 are connected or fluidly communicated with one another via the tube 20. The priming solution P from the feed bag 6 is fed to the blood reservoir 3 by way of the tube 20.

The tube 92 is connected to the connecting port 35. The blood reservoir 3 and the pump 4 are connected via the tube 92. A liquid (blood B or priming solution P) is fed from the blood reservoir 3 to the oxygenator 5 by the operation of the oxygenator.

In use, the blood reservoir 3 is positioned so that the connecting ports 36, 37 are located at the vertically upper part of the reservoir while the connecting port 35 is located at the lower part of the reservoir.

The tube 381 is connected to the connecting port 37 and extends downwardly inside the housing 33. This allows the tube 381 to communicate with the tube 91 on the upper end side of the reservoir via the connecting port 37. Further, the lower end 381a of the tube 381 is open. As shown in FIG. 12, the lower end 381a is located in the vicinity of the bottom 312 of the housing projection 311, and faces the bottom 312.

As illustrated in FIG. 12, a filter member 382 is disposed outside the tube 381. The filter member 382 is in the shape of a sack and sheathes the tube 381. The upper end of the filter member 382 is supported by the cover 32. The filter member 382 removes foreign matter or bubbles in blood. The filter member 382 is preferably formed of a porous material having sufficient blood permeability.

A filter member 392 in the shape of a sack is disposed on the housing 33 side of the connecting port 36. The upper end of the filter member 392 is supported by the cover 32. The filter member 392 removes foreign matter or bubbles in the priming solution P, transfusional blood, or a replacement fluid. The material from which the filter member 392 is preferably formed is a porous material having sufficient priming solution (liquid) permeability.

Antifoaming members are preferably also provided. These antifoaming members are preferably positioned between the tube 381 and the filter member 382, and inside the filter member 392.

The material forming the tube 381 is not particularly limited. Examples of suitable materials may include polymer materials such as polycarbonate, acrylic resin, polyethylene terephthalate (PET), polyethylene, polypropylene, and polyvinyl chloride.

Further, examples of the porous material forming the filter members 382, 392 may include mesh-like ones, a woven fabric, and a nonwoven fabric. These may be used alone, or in given combination (particularly in lamination) thereof.

The oxygenator 5 performs gas exchange with respect to blood B. As shown in FIG. 1 (and in FIGS. 2-11), the oxygenator 5 includes a blood inflow port 512 through which blood flows into the oxygenator 5, a blood outflow port 513 through which blood flows out of the oxygenator 5, a gas inflow port 514 through which oxygen gas flows therein, a gas outflow port through which unnecessary gas is discharged, a heat carrier inflow port 515, and a heat carrier outflow port 516. The ports 512, 513, 514, 515, 516 project outwardly from the housing of the oxygenator 5. The oxygenator 5 also includes a hollow fiber membrane bundle. The hollow fiber membrane bundle is housed in the housing of the oxygenator and is comprised of a large number of integrated hollow fiber membranes adapted to perform a gas exchange function in a known manner. Further, a filter member may be disposed at the periphery of the hollow fiber membrane bundle,. This filter is configured to trap bubbles.

The pump 4 transfers blood in the extracorporeal circuit 1 (circuit body 9). The pump 4 has a rotator which rotates under the control of a control device. The pump 4 can adjust the quantity of transferred liquid according to the number of rotations of the rotator. The pump 4 is disposed between the blood reservoir 3 and the oxygenator 5, and is connected to the tube 92 connected to the blood reservoir 3 and the tube 93 connected to the oxygenator 5 as shown by way of example in FIG. 1.

As described above, the circuit body 9 includes the tubes 90, 92, 93, 96. Further, the tube 90 can be divided into three regions or portions, namely the tubes 91, 94, 95. As shown in FIG. 1, as well as FIGS. 2 and 3, the circuitry of the extracorporeal circuit 1 is configured such that the tube 91 serving as a venous line during extracorporeal circulation, the blood reservoir 3, the tube 92, the pump 4, the tube 93, the oxygenator 5, the tube 94 serving as an arterial line during extracorporeal circulation, and the tube 95 serving as a linkage line linking the ends of the tubes 91, 94, are connected in this order.

Figure 3:
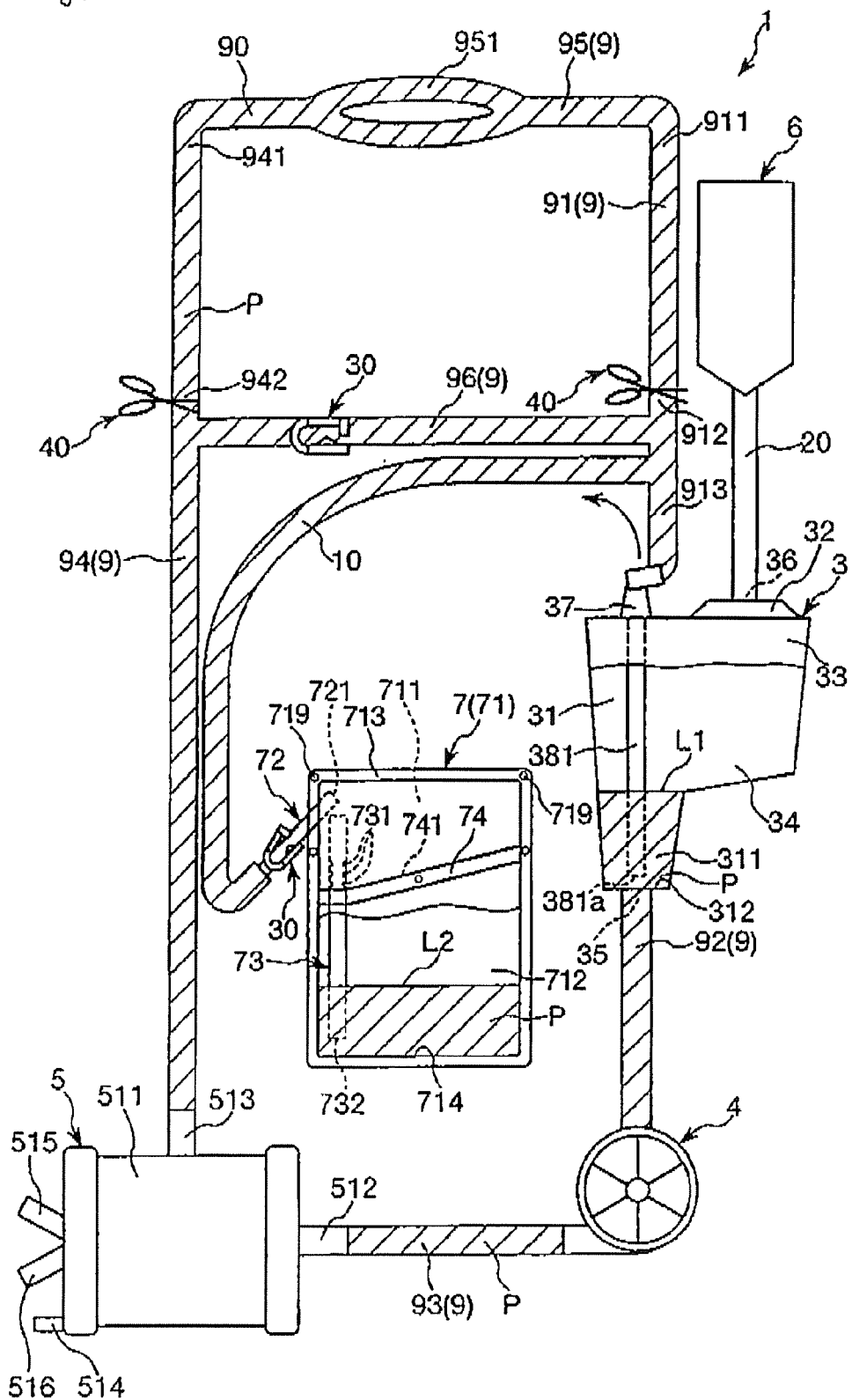
FIG. 3 is a schematic illustration of the circuitry of the extracorporeal circuit illustrated in FIG. 1 showing another aspect of the manner of use of the disclosed extracorporeal circuit.
Figure 5:
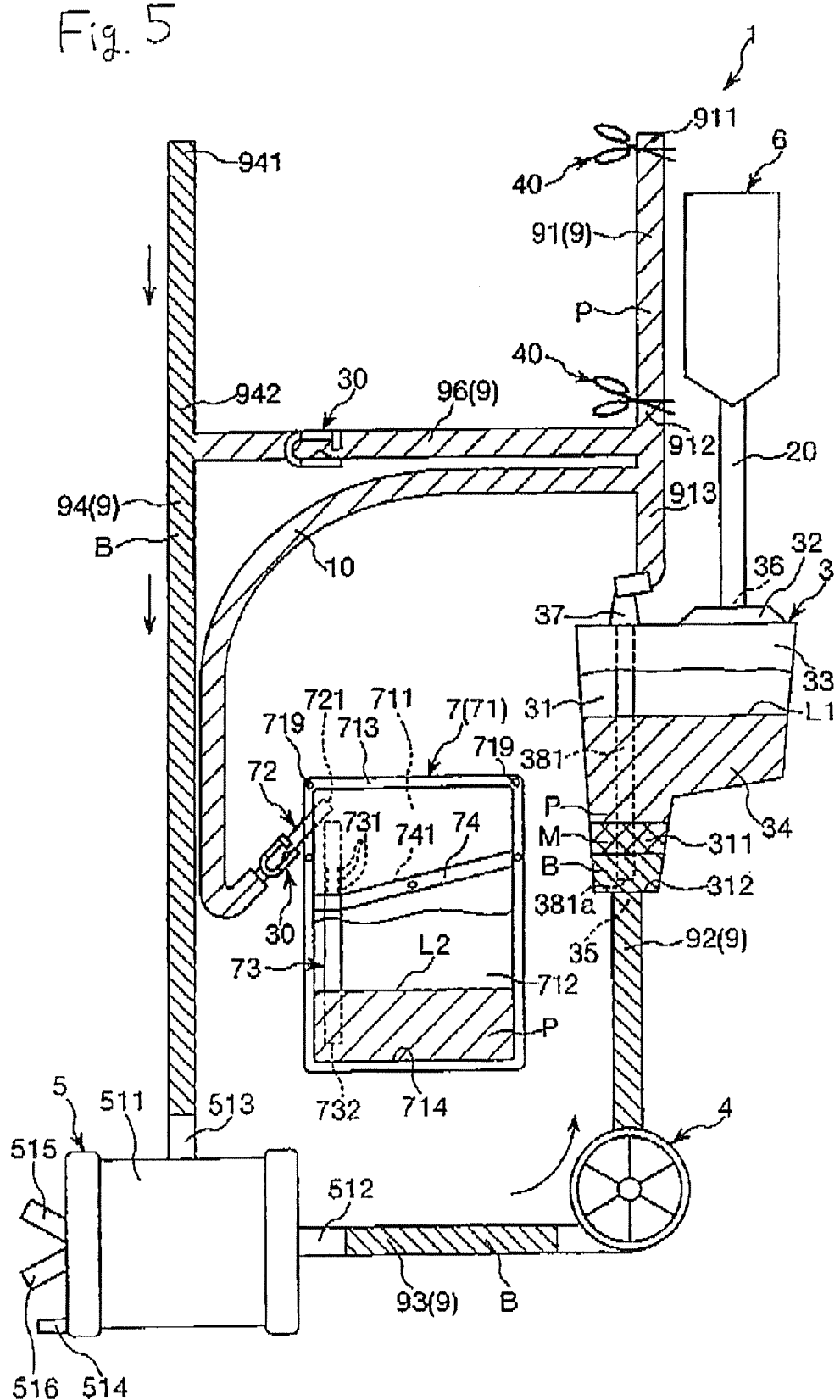
FIG. 5 is a schematic illustration of the circuitry of the extracorporeal circuit illustrated in FIG. 1 showing a further aspect of the manner of use of the disclosed extracorporeal circuit.

The tube 95 is set in the extracorporeal circuit 1 until the extracorporeal circuit 1 is primed with the priming solution P as shown for example in FIG. 3. Thereafter, as shown in FIG. 5 (similarly in FIGS. 6-11), when blood B is extracorporeally circulated, a part of the tube 95, for example between the central part of a loop 951 of the tube 95 and a portion on the tube 94 side is cut and removed. The remaining parts thereof are connected to catheters previously indwelled in a patient, respectively. In this state, extracorporeal circulation of blood B is performed.

Further, in the extracorporeal circuit 1, an intermediate portion (middle) of the tube 91 and an intermediate portion (middle) of the tube 94 are linked by the tube 96. The tube 96 functions as a recirculation line when recirculation of blood B is carried out at the extracorporeal circuit 1.

The tube 10 is connected to the tube 91 at a position between the point where the tube 91 is connected to the tube 96 and the point where the tube 91 is connected to the reservoir 3. The tube 10 is connected with the collection bag 7. In the illustrated embodiment, the tube 10 is connected to the collection bag 7 by way of an inlet tube 72. The tube 10 and the inlet tube 72 together constitute a line connecting the collection bag 7 to the tube 91. The priming solution P passes through the tube 10 to be collected into the collection bag 7. The configuration of the collection bag 7 will be described later.

The clamps 30 are set at intermediate regions (e.g., middle) of the tube 96 and an inlet tube 72 of the collection bag 7. The clamps 30 can press and close the respective tubes. This brings the tube 96 (similarly for the inlet tube 72) into the closed state. When the pressed and closed state of the clamp 30 is released, the tube 96 (similarly for the inlet tube 72) is in an opened state. Instead of positioning the clamp 30 in the intermediate region (e.g., middle) of the inlet tube 72 of the collection bag 7, the clamp 30 may be set in an intermediate region (e.g., middle) of the tube 10.

The amount of priming solution P to be fed is preferably 750 to 1500 mL when the lengths of the tubes 91, 94 occupying the most part of the circuit body 9 are respectively, for example, 100 to 200 cm.

Examples of the priming solution P may include physiological saline and a lactated Ringer's solution.

The collection container (collection bag) 7 is adapted to collect the priming solution P. As shown in FIGS. 1-11, the collection bag 7 is disposed at a vertically lower position than the blood reservoir 3 during use, whereby the bottom wall of the collection container 7 is vertically lower than (vertically below) the bottom wall of the reservoir 3. More specifically, in setting the height of the collection bag 7, the height of the opening 721 of the inlet tube 72 is aligned with the height of the objective liquid level L1 (in the state shown in FIG. 3, as well as FIG. 7) in the blood reservoir 3 to such a degree as to enable collection of the priming solution P from the blood reservoir 3 according to the principle of a siphon described later. This causes a difference in pressure between the pressure applied on the priming solution P in the blood reservoir 3 and the pressure applied on the priming solution P of the opening 721. Namely, according to the principle of a siphon, the priming solution P can be transferred from the blood reservoir 3 to be collected into the collection bag 7 with reliability (compare, for example, the state shown in FIG. 2 to the state shown in FIG. 3).

The method of adjustment of the setting height of the collection bag 7 is not particularly restricted. However, for example, in this embodiment, adjustment thereof can be carried out by the collection bag support device 8 shown in FIG. 13.

The collection container (collection bag) 7 comprises a bag body 71 formed of a sack body, the inlet tube (introduction part) 72 provided on the bag body 71, and a communication tube 73 constituting a communication part. The collection container is flexible in that it possesses flexible side walls.

As shown in FIG. 14, the bag body 71 is in the shape of a rectangle in plan configuration. The bag body 71 is configured as follows. As with the bag 6, two sheet materials having flexibility made of soft resin such as polyvinyl chloride are stacked. The peripheries of the two sheets are fused or bonded in a band to form a fused part 713, resulting in a sack form. Further, the space (the inside of the sack body) formed between the sheet materials is divided into a first space 711 and a second space 712 in the longitudinal direction (the vertical direction in FIG. 14) by a partition part 74. The first space 711 communicates with the inlet tube 72 so that the priming solution P is introduced into the space 711 from the tube 10. The inlet tube 72 thus constitutes an introduction part. The first space 711 and the second space 712 communicate with each other via the communication tube 73.

As shown in FIG. 13 (as well as FIGS. 1-11), the posture or orientation of the collection bag 7 during use is such that the first space 711 is located above (vertically/elevationally higher) the second space 712. As a result of this, the priming solution P introduced into the first space 711 via the inlet tube 72 passes through the communication tube 73, and is reliably collected into the second space 712 as generally seen in FIG. 14. The volume of the second space 712 is set almost equal to or slightly larger than the volume of the bag 6.

The volume of the first space 711 is smaller than the volume of the second space 712. In the bag body 71, the priming solution P is not stored in the first space 711. Therefore, the first space 711 is the dead space of the bag body 71. The smaller volume of the first space 711 relative to the second space 712 helps enable the proportion occupied by the dead space, i.e., the first space 711 with respect to the whole bag body 71, to be suppressed. Thus, this configuration contributes to the size reduction of the bag body 71.

The partition part 74 that divides the inside of the bag body 71 into the first space 711 and the second space 712 can be formed by fusing the sheet materials forming the bag body 71 in a band as with the fused part 713. In other words, as mentioned above, the bag body can be formed by two sheets of material fused together along their peripheries. The partition plate 74 can be provided by fusing together the two sheets in the area corresponding to the desired location of the partition plate 74.

The partition part 74 is configured and oriented such that the part defining the first space 711 is an inclined or tilted part 741. The priming solution P introduced into the first space 711 flows downwardly in the direction of tilt of the tilted part 741. Further, the communication tube 73 is located at the lower part in the direction of tilt of the tilted part 741. This prevents the priming solution P flowing toward the communication tube 73 along the tilt part 741 from remaining in the first space 711. The priming solution P flows into the second space 712 via the communication tube 73 (see FIG. 14).

A plurality of suspending parts 719 are provided in the bag body 71. The suspending parts 719 suspend the collection bag 7 on the collection bag support device 8. In the illustrated embodiment, respective suspending parts 719 are formed of holes formed in the fused part 713 and the partition part 74. A prescribed suspending part 719 of these suspending parts 719 is hung on the collection bag support device 8. This can brings the collection bag 7 into such a state that the first space 711 is situated above the second space 712 (suspended state). This enables the use of the collection bag in this state as shown in FIG. 13. The site at which each suspending part 719 is formed has no particular restriction. However, examples of the site may include the upper end corner portion of the fused part 713 or an intermediate part (middle) thereof, an intermediate portion (middle) of the partition part 74, and the crossing part of the partition part 74 and the fused part 713.

As shown in FIG. 14, the inlet tube 72 is set at the upper end part of the bag body 71. The inlet tube 72 serves as a member for introducing the priming solution P from the tube 10 into the first space 711.

An intermediate part (e.g., middle) of the inlet tube 72 is supported and fixed to a part of the fused part 713 of the bag body 71. Further, the inlet tube 72 is fixed in an inclined state. The inclined inlet tube 72 is configured such that the opening 721 is located in the first space 711, and an opening 722 is present on the opposite side from the opening 721. The bore part 723 of the inlet tube 72 communicates with the first space 711 via the opening 721. Further, the tube 10 is connected to the opening 722. Thus, the priming solution P which has passed through the tube 10 flows into the bore part 723 of the inlet tube 72 via the opening 722.

As described above, the inlet tube 72 is fixed in an inclined state. Accordingly, the opening 721 is upwardly opened. When the opening 721 of the inlet tube 72 is downwardly opened, for example, when droplets drop from the opening 721, air unfavorably enters the inlet tube 72 in an amount equivalent to the dropped droplets. In order to prevent the occurrence of such a problem, it is preferable that the direction in which the opening 721 of the inlet tube 72 is opened is controlled or regulated.

In this illustrated embodiment, the opening 721 is upwardly opened. However, the configuration of the opening 721 is not limited thereto. For example, the opening 721 may be opened toward the horizontal direction.

The communication tube 73 is located at the vertically lower part of the opening 721 of the inlet tube 72. As a result of this, when the priming solution P flows into the first space 711 via the inlet tube 72, the priming solution P quickly flows into the communication tube 73.

The material for forming the inlet tube 72 is not particularly limited. However, the same material as that used for the housing body 31 of the blood reservoir 3 can be used.

As shown in FIG. 14, the communication tube 73 is set in the bag body 71 in such a manner as to extend in both the first space 711 and the second space 712. The priming solution P in the first space 711 flows into the second space 712 via the communication tube 73.

The communication tube 73 is supported and fixed at its intermediate (middle) portion to a part of the partition part 74. Further, the communication tube 73 is fixed in such an orientation that the longitudinal direction of the tube 73 is the vertical direction in the use state (suspended state) of the collection bag 7.

A plurality of side holes 731 opening toward the first space 711 are formed in the wall part (tube wall) of the communication tube 73. Respective side holes 731 are located in the vicinity of the partition part 74, on the upper side of the partition part 74. The priming solution P in the first space 711 flows into the bore part 733 of the communication tube 73 via the side holes 731. Then, the priming solution P is collected in the second space 712 via the lower end opening 732 (the end on the second space 712 side). The flow of the priming solution P is indicated with an arrow in FIG. 14.

The communication tube 73 extends to the vicinity of the bottom 714 of the bag body 71. Thus, the lower end opening 732 is located in the vicinity of the bottom 714.

The upper end 734 of the communication tube 73 is open in the manner shown in FIG. 14. However, the configuration of the upper end of the communication tube 73 is not limited in that regard, and the upper end 734 of the communication tube 73 may be closed.

The material for forming the communication tube 73 is not particularly limited. However, as an example, the same material as that used for the housing body 31 of the blood reservoir 3 can be used.

When the collection bag 7 is the unused state, i.e., in such a state that the priming solution P has not yet been collected, generally the portions (which are hereinafter referred to as "space defining parts 712*a*") of the respective sheet materials forming the bag body 71 defining the second space 712 are in close contact with each other. From this state, according to the principle of a siphon (the difference in height of the liquid level L1 of the priming solution P in the blood reservoir 3 from the opening 721 of the collection bag 7), the priming solution P in the blood reservoir 3 is once introduced into the first space 711 via the inlet tube 72. Then, the introduced priming solution P is collected in (flows into) the second space 712 via the communication tube 73. At this time, the bonded space defining parts 712*a* start to be separated from each other. Therefore, the volume of the second space 712 increases, and the pressure (internal pressure) of the inside of the second space 712 decreases. In the collection bag 7, the first space 711 and the second space 712 are divided by the partition part 74. Therefore, the first space 711 is prevented (or inhibited) from receiving the effects of the decrease in pressure of the second space 712. For this reason, the internal pressure of the first space 711 does not substantially change. As used here, the phrase "the internal pressure of the first space 711 does not substantially change" denotes that the change ratio of the internal pressure of the first space 711 is 0 to 5%.

With a conventional collection bag configured such that two sheet materials having flexibility are simply fused at the edges thereof to form only one space (storage space), when a priming solution flows into the space, the pressure of the inside of the space decreases. Then, the priming solution is drawn (collected) into the collection bag excessively (involuntarily) by virtue of this increase in pressure.

Here though, even when the priming solution P is collected in the collection bag 7 as described above, a substantial change in the internal pressure of the first space 711 into which the priming solution P is introduced does not occur. Therefore, excessive collection of the priming solution P is prevented with reliability. Stated differently, the collection of priming solution P in the bag 7 can better controlled.

As described above, the lower end opening 732 of the communication tube 73 is located in the vicinity of the bottom 714. Therefore, in a relatively early period from start of flow of the priming solution P into the second space 712, the height of the liquid level L2 of the priming solution P in the second space 712 exceeds the height of the lower end opening 732 of the communication tube 73 as shown in FIG. 14. In this state, communication between the part of the second space 712 except for the priming solution P and the first space 711 is blocked by the priming solution P in the second space 712. As a result, even when the pressure of the part of the second space 712 except for the priming solution P changes (increases or decreases), the first space 711 does not experience (i.e., does not receive or is not subjected to) the effect of the change. As a result, a substantial change does not occur in the internal pressure of the first space 711. This helps prevent the priming solution P in the inlet tube 72 (tube 10) from being involuntarily thrust back, nor being drawn. As a result, the priming solution P can be collected in the proper quantity in the collection bag 7.

Thus, collection of the priming solution P can be carried out in a desirable manner.

As described above, the collection bag 7 is supported to the collection bag support device 8 during use (the collection bag support device 8 is omitted from illustration in FIGS. 1-11). As shown in FIG. 13, the collection bag support device 8 includes a base 81, a column 82 supported at its lower end by the base 81, a moving member 83 mounted on the column 82 to move in the longitudinal direction along the column 82, two hooks 84 supported by the moving member 83, and a setscrew 85 for fixing the moving member 83 to the column 82. These respective members can be formed of, for example, various metal materials or various resin materials.

The base 81 is a member in the shape of a flat plate. The base 81 has a size and a weight of such a degree as to prevent the collection bag support device 8 from tilting even when the collection bag 7 is supported on the collection bag support device 8.

The column 82 has a cylindrical outer shape.

The moving member 83 is formed of an elongated member, and has a hole 831 at one of its ends that allows the column 82 to be inserted therethrough. The side part of the moving member 83 is provided with a threaded through hole that communicates with the hole 831.

Each hook 84 possesses an L-shape. Further, the hooks 84 are spaced apart from each other along the longitudinal extent of the moving member 83. By inserting respective hooks 84 into the suspending parts 719 of the collection bag 7, the collection bag 7 can be suspended and used in the suspended state.

The setscrew 85 includes a male screw part 851, and a head part 852 at one end of the male screw part 851. The male screw part 851 screws into the threaded through hole of the moving part 83 so that the end of the male screw part 851 opposite the head part 852 engages (contacts) the outer circumferential surface of the column 82. As a result, the moving member 83 can be fixed in position along the vertical extent of the column 82. Accordingly, the collection bag 7 can be held at a prescribed position (height).

By loosening the setscrew 85, the moving member 83 is released and can be moved. As a result, the setting height of the collection bag 7 with respect to the blood reservoir 3B can be changed.

Thus, the extracorporeal circuit 1 is configured such that the setting height of the collection bag 7 with respect to the blood reservoir 3 can be adjusted by movement of the moving member 83 of the collection bag support device 8. As a result, the amount of the priming solution P to be collected in the collection bag 7 can be appropriately set as desired.

The column 82 has a cylindrical outer shape. As a result, when the setscrew 85 is released to allow the moving member 83 to be moved, the moving member 83 is able to rotate about the shaft of the column 82. This can change the orientation of the held collection bag 7 according to, for example, the standing position of the user. As a result, the collection state of the priming solution P to be collected in the collection bag 7 can be visually observed with relative ease.

One example of a method for using the extracorporeal circuit 1 described above is now set forth. Initially, it is assumed that the tube 20 has not yet been connected to the feed bag 6 filled with the priming solution P.

In the initial state shown in FIG. 1, the pump 4 is stopped. The clamp 30 disposed along the tube 96 is in the open state, and the clamp 30 disposed along the inlet tube 72 of the collection bag 7 is in a closed state.

Three forceps 40 (each individual forceps 40 is referred to as a pair of forceps) are applied to the tube 91 in this initial state. Referring to FIG. 1, the setting site for one pair of the forceps 40 is between the place where the tube 91 joins the tube 95 and the place where the tube 91 joins the tube 96, but closer to the tube 95 (i.e., adjacent the tube 95). The setting site for a second pair of the forceps 40 is also between the place where the tube 91 joins the tube 95 and the place where the tube 91 joins the tube 96, but closer to the tube 96 (i.e., adjacent the tube 96). The setting site of a third pair of the forceps 40 is between the point where the tube 91 joins the tube 96 (the tube 10) and the point where the tube 91 joins the blood reservoir 3. Hereinafter, the parts of the tube 91 to which respective forceps 40 are set are referred to as the "forceps-attached part 911", the "forceps-attached part 912", and the "forceps-attached part 913" sequentially from the tube 95 side (the top side in FIG. 1).

Two additional forceps 40 are provided in the initial state and are set to the tube 94. The setting site of one pair of forceps 40 is, in the circuitry shown in FIG. 1, between the place where the tube 94 joins the tube 95 and the place where the tube 94 joins the tube 96, but closer to the tube 95 (i.e., adjacent the tube 95). The setting site of the other pair of forceps 40 is between the place where the tube 94 joins the tube 95 and the place where the tube 94 joins the tube 96, but closer to the tube 96 (i.e., adjacent the tube 96). Hereinafter, the parts of the tube 94 to which respective pairs of forceps 40 are set are referred to as the "forceps-attached part 941" and the "forceps-attached part 942" sequentially from the tube 95 side (the top side of FIG. 1).

The collection bag 7 is set on (supported or hung on) the collection bag support device 8. The setting height of the collection bag 7 is set such that the height of the opening 721 of the collection bag 7 is aligned with the objective height of the liquid level L1 (shown in FIG. 3 or 7) in the blood reservoir 3. Using the collection bag support device 8, the height of the collection bag 7 is adjusted to be such a height.

The height of the collection bag 7 is thus set. This allows the priming solution P to be collected into the collection bag 7 relatively easily and quickly according to the principle of a siphon to be described later.

Next, all of the pairs of forceps 40 are removed, and the tube 20 is connected to the bag 6. As a result, the priming solution P in the bag 6 flows into the blood reservoir 3 through the tube 20 by its own weight, and further, flows in the direction of the arrow of FIG. 2. Further, at this time, the pump 4 is also operated.

When the tube 20 is connected to the bag 6, the priming solution P in the bag 6 first passes through the tube 20 and the connecting port 36 of the blood reservoir 3 sequentially, and is introduced into the housing 33. The priming solution P introduced in the housing 33 flows out of the connecting port 35. The priming solution P then sequentially passes through the tube 92, the pump 4 and the tube 93, and is fed to the oxygenator 5. The priming solution P further passes through the oxygenator 5, and flows into the tube 94. The priming solution P flowing into the tube 94 is divided into two flows, one directed toward the tube 96 from the middle of the tube 94, and the other which continues flowing along the tube 94 to the end (downstream side) of the tube 94 where it is directed toward the tube 95.

The priming solution P directed toward the tube 96 from the middle of the tube 94 sequentially passes through the tube 96 and the tube 91, and flows back into the blood reservoir 3. Further, the priming solution P which is directed towards the tube 95 passes through the tube 95 and the tube 91 sequentially, and merges into the priming solution P from the tube 96 in the middle of the tube 91, and flows into the blood reservoir 3 again. Then, the liquid level L1 of the priming solution P in the blood reservoir 3 lies at an elevationally higher position than the position of the opening 72 of the collection bag 7.

The priming solution P passing through the tube 91 partly flows into the blood reservoir 3, and partly branches from the tube 91 and flows from the tube 10 even to the portion of the inlet tube 72 closed by the clamp 30. As a result, as shown in FIG. 2, the inside of the tube 10 is filled with the priming solution P which has flowed into the tube 10.

Through the foregoing process, the entire extracorporeal circuit 1, except for the bag 6 and the tube 20, is filled with the priming solution P. That is, the entire extracorporeal circuit 1, except for the bag 6 and the tube 20, is primed. Also, in the extracorporeal circuit 1, the liquid level L1 of the liquid, including the priming solution P (or the blood B when it is introduced into the blood reservoir as discussed below), in the blood reservoir 3 is set so as to be invariably located above the lower end 381a of the tube 381 (see FIGS. 2-11). As a result, when the priming solution P in the blood reservoir 3 is collected, the principle of a siphon can be applied (used).

Further, as described above, the inlet tube 72 of the collection bag 7 is closed by the clamp 30. This prevents the priming solution P in the tube 10 from flowing into the collection bag 7. As a result, the priming solution P in the extracorporeal circuit 1 can be prevented from being collected in the collection bag 7 involuntarily, namely before priming of the entire extracorporeal circuit 1.

Figure 2:
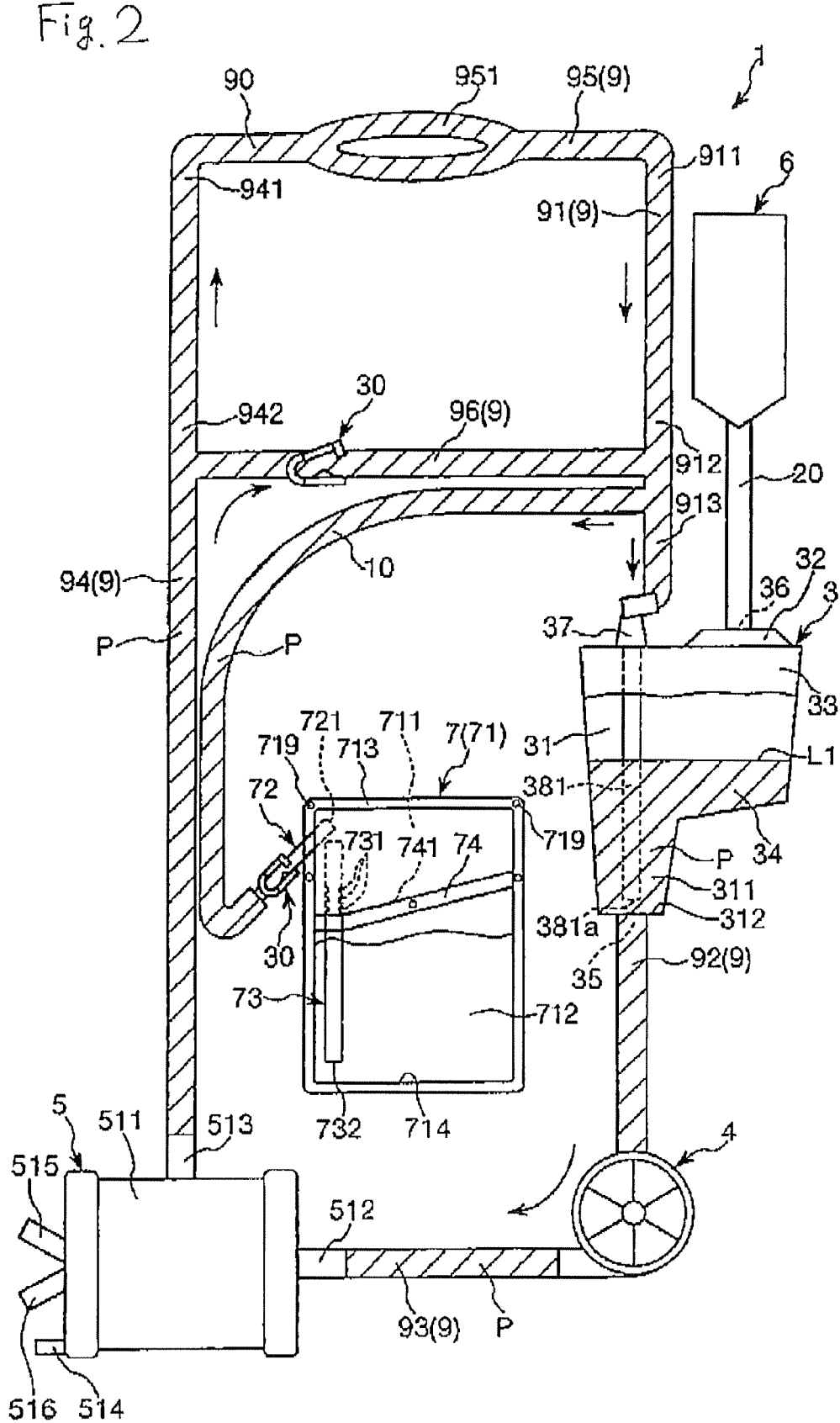
FIG. 2 is a schematic illustration of the circuitry of the extracorporeal circuit illustrated in FIG. 1 showing another aspect of the manner of use of the disclosed extracorporeal circuit.

In the state shown in FIG. 2, it is preferable to transfer as much of the priming solution as possible to the collection bag 7. However, it is also desirable to keep a certain amount (level) of priming solution in the blood reservoir to avoid air intrusion into the extracorporeal circuit. The precise volume of fluid which should be retained to avoid air intrusion is not a precise or specific amount, but should preferably be 100-200 ml. Stated differently, the amount of priming solution P at the level L1 in FIG. 2 minus the amount of priming solution at the level L1 in FIG. 3 represents the unnecessary or excessive priming solution which should be transferred to the collection bag 7. In the subsequent operation following FIG. 2, this unnecessary portion of the priming solution is transferred to and collected in the collection bag 7.

As shown in FIG. 3, the clamp 30 set on the tube 96 is rendered in a closed state. Further, the forceps 40 are set to the forceps-attached part 912 of the tube 91, and the forceps 40 are set to the forceps-attached part 942 of the tube 94. Further, at this time, the operation of the pump 4 is stopped.

Thereafter, the clamp 30 on the inlet tube 72 of the collection bag 7 is rendered in an open state (i.e., is opened) As a result, the tube 91 and the bag body 71 communicate with each other via the tube 10 and the inlet tube 72. As a result, by the difference in height of the liquid level L1 in the blood reservoir 3 from the opening 721 of the collection bag 7, namely, based on the siphon principle, the priming solution P is transferred to and collected in the collection bag 7 in the following manner. This is shown by a comparison of FIGS. 2 and 3. As described above, the opening 721 of the collection bag 7 is located at the height of the objective liquid level.

When the clamp 30 on the inlet tube 72 is opened (rendered in an open state), by virtue of the difference in pressure between the pressure (atmospheric pressure) applied on the liquid level L1 of the priming solution P in the housing body 31 and the pressure applied on the distal end of the priming solution P in the inlet tube 72, the priming solution P in the housing body 31 passes through the tube 381 and is introduced into the tube 91. Then, the priming solution P introduced in the tube 91 flows in the direction in which it can flow, i.e., toward the tube 10. This causes the priming solution P to flow (to be collected) into the collection bag 7. Such a phenomenon continues until the liquid level L1 in the blood reservoir 3 is located at the same height as that of the opening 721 of the collection bag 7, i.e., the difference in height is eliminated (the principle of a siphon). As a result, the unnecessary portion of the priming solution P in the blood reservoir 3 can be collected readily and quickly. Further, as described above, in the collection bag 7, the change in internal pressure of the first space 711 can be inhibited which helps enable the priming solution P to be collected into the collection bag 7.

Thus, with the extracorporeal circuit 1, so long as the height of the opening 721 of the collection bag 7 is appropriately adjusted, the priming solution P in the amount corresponding thereto flows into the collection bag 7. As a result, when the extracorporeal circuit 1 is operated, an operator is not required to carry out the operation while observing the position of the liquid level L1 in the blood reservoir 3.

Figure 4:
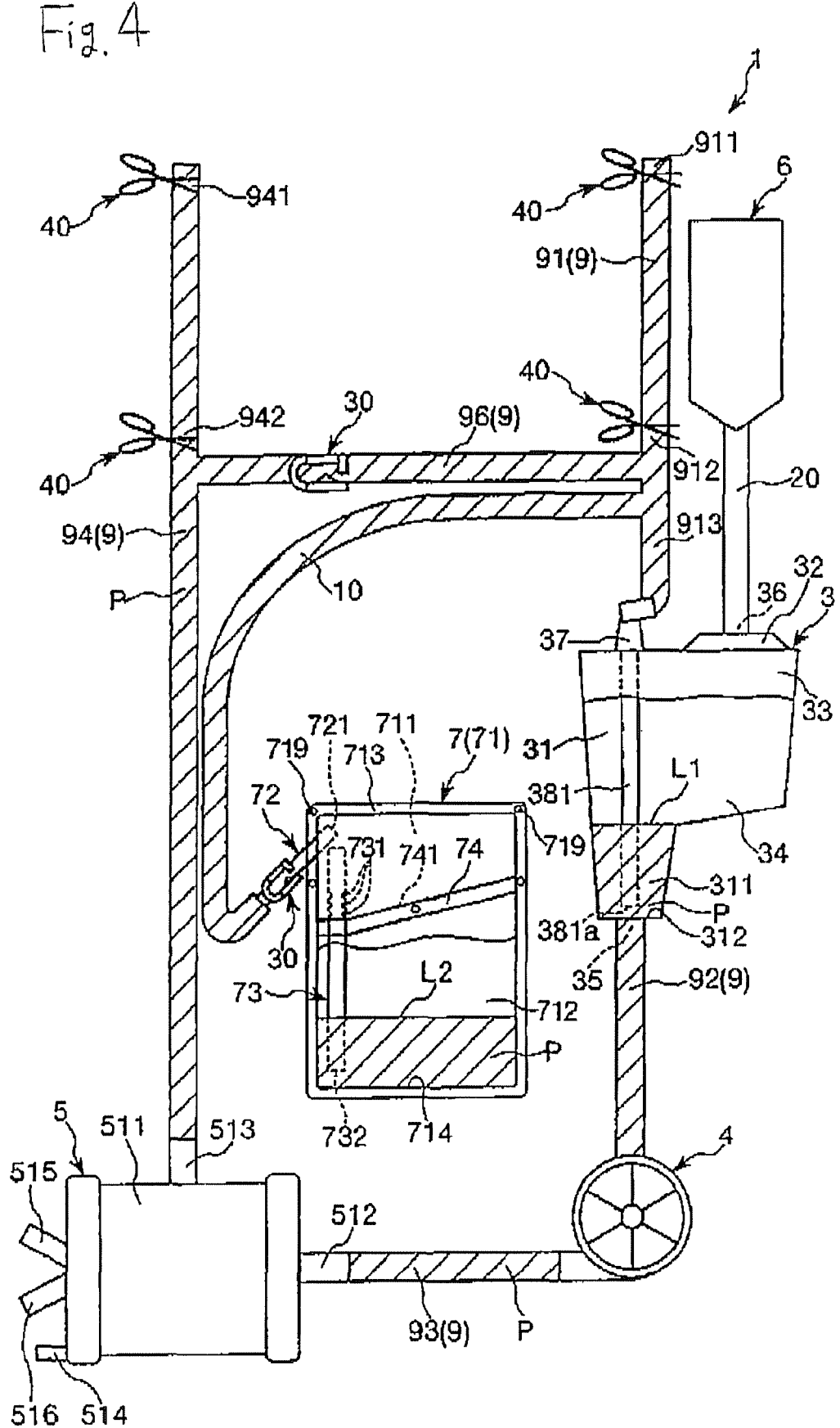
FIG. 4 is a schematic illustration of the circuitry of the extracorporeal circuit illustrated in FIG. 1 showing another aspect of the manner of use of the disclosed extracorporeal circuit.

After the priming solution P is thus collected, the clamp 30 set to the inlet tube 72 is rendered in a closed state again as shown in FIG. 4. Further, the forceps 40 are attached to the forceps-attached part 911 of the tube 91, and the forceps 40 are attached to the forceps-attached part 941 of the tube 94.

In such a state, as described above, the tube 95 is cut, and is connected to the arterial-line catheter of the two catheters previously indwelled in a patient.

From the state shown in FIG. 4, two pairs of forceps 40 of the tube 94 (forceps-attached parts 941 and 942) are removed, respectively. At this step, blood B flows in the direction of the arrow in FIG. 5 into the tube 94 from the patient via the arterial-line catheter due to the blood pressure and the difference in height. The flow of the blood B is opposite to that in normal extracorporeal circulation.

The blood B which has flowed into the tube 94 further passes through the oxygenator 5, the tube 93, the pump 4, and the tube 92 sequentially, and flows into the projection 311 of the housing 33 via the connecting port 35 of the blood reservoir 3. The blood B thrusts the priming solution P in the tube 94, the oxygenator 5, the tube 93, the pump 4, and the tube 92 into the housing 33. In other words, the priming solution P in the tube 94, the oxygenator 5, the tube 93, the pump 4, and the tube 92 is replaced with the blood B.

Further, when the blood B flows into the projection 311, the blood B is mixed with the priming solution P in the projection 311. Namely, by virtue of the blood B, a part of the priming solution P in the projection 311 is colored red, but lighter than the red color of the blood B. The part located between the priming solution P and the blood B in the projection 311 in FIG. 5 denotes a liquid mixture M including the priming solution P and the blood B mixed together.

Figure 6:
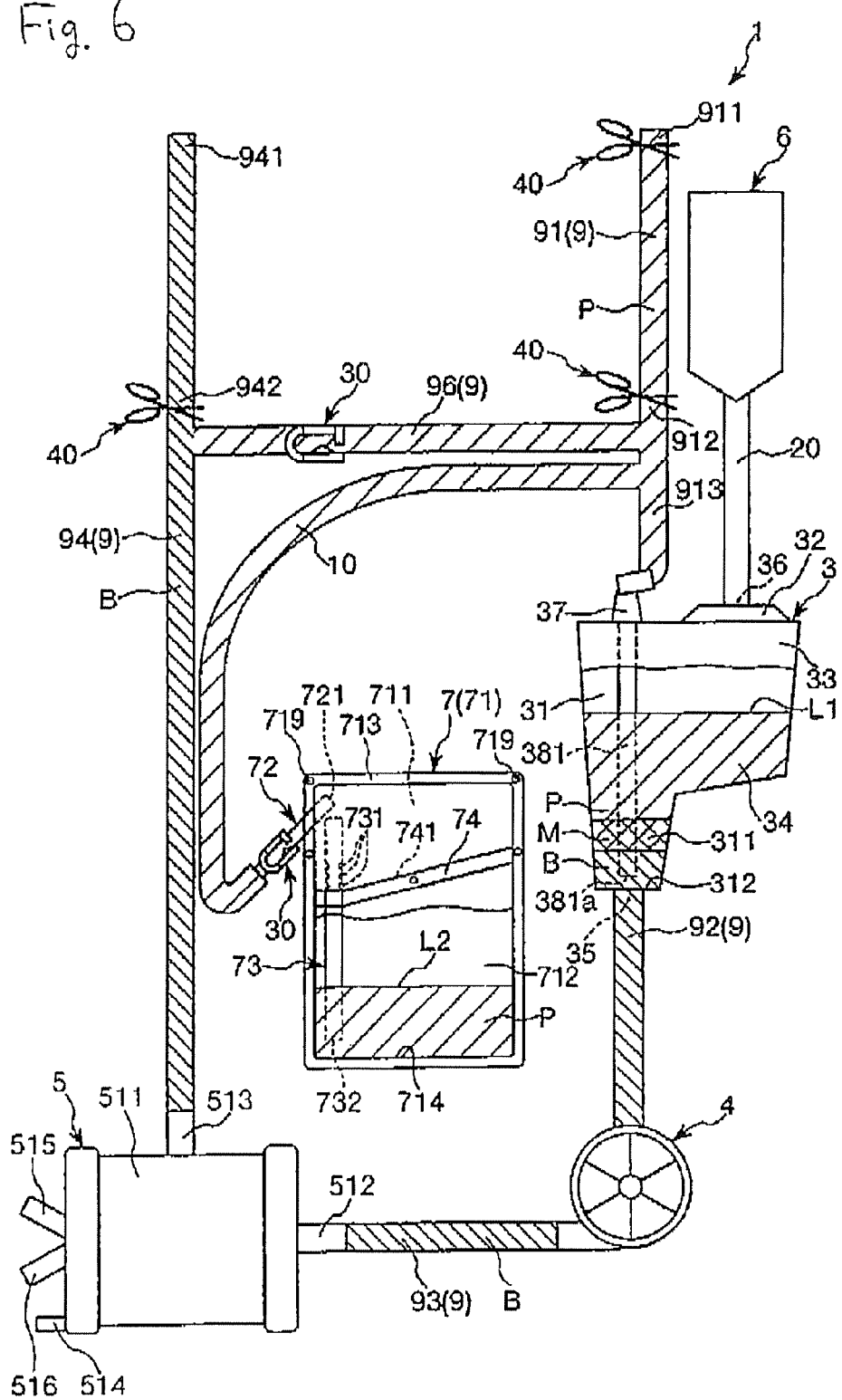
FIG. 6 is a schematic illustration of the circuitry of the extracorporeal circuit illustrated in FIG. 1 showing another aspect of the manner of use of the disclosed extracorporeal circuit.

After such coloring is observed, the forceps 40 are set to the forceps-attached part 942 of the tube 94 again as illustrated in FIG. 6. This stops the blood B from flowing into the tube 94. Further, the rise of the liquid level L1 in the blood reservoir 3 is accordingly also stopped.

In the state shown in FIG. 6, the priming solution P present in the tube 94, the oxygenator 5, the tube 93, the pump 4, and the tube 92 remains in the blood reservoir 3. Further, the priming solution P is left between the tube 381 in the blood reservoir 3 and the part of the tube 91 to which the tube 10 is connected. In the subsequent step, the unnecessary portion of the priming solution P is collected into the collection bag 7.

Figure 7:
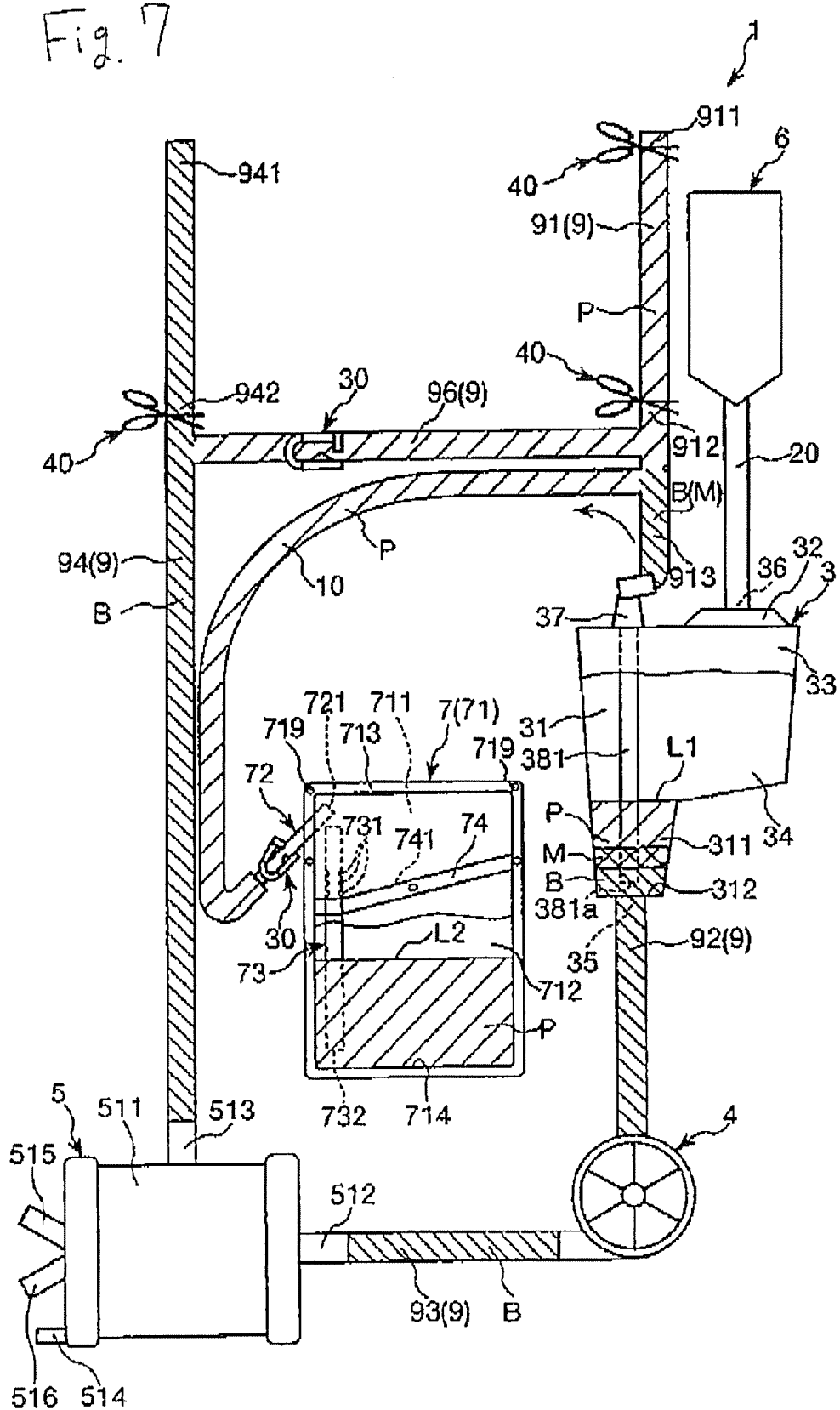
FIG. 7 is a schematic illustration of the circuitry of the extracorporeal circuit illustrated in FIG. 1 showing another aspect of the manner of use of the disclosed extracorporeal circuit.

From the state shown in FIG. 6, the clamp 30 set to the inlet tube 72 of the collection bag 7 is rendered in an open state again as illustrated in FIG. 7. As a result, almost as with the aspect of the operation described earlier, the priming solution P (also including the liquid mixture M) in the blood reservoir 3, and the priming solution P between the tube 381 in the blood reservoir 3 and the part of the tube 91 to which the tube 10 is connected, flow into the collection bag 7 through the tube 10. Incidentally, the inflow of the priming solution P continues until the liquid level L1 in the blood reservoir 3 is situated at the same height as that of the opening 721 of the collection bag 7.

Thus, by a simple operation in which the clamp 30 is rendered in an open state, the unnecessary amount of the priming solution P can be collected readily and quickly. Further, also in this operational aspect, in the collection bag 7, the change in internal pressure of the first space 711 is inhibited or prevented, and hence the priming solution P can be collected into the collection bag 7.

Figure 8:
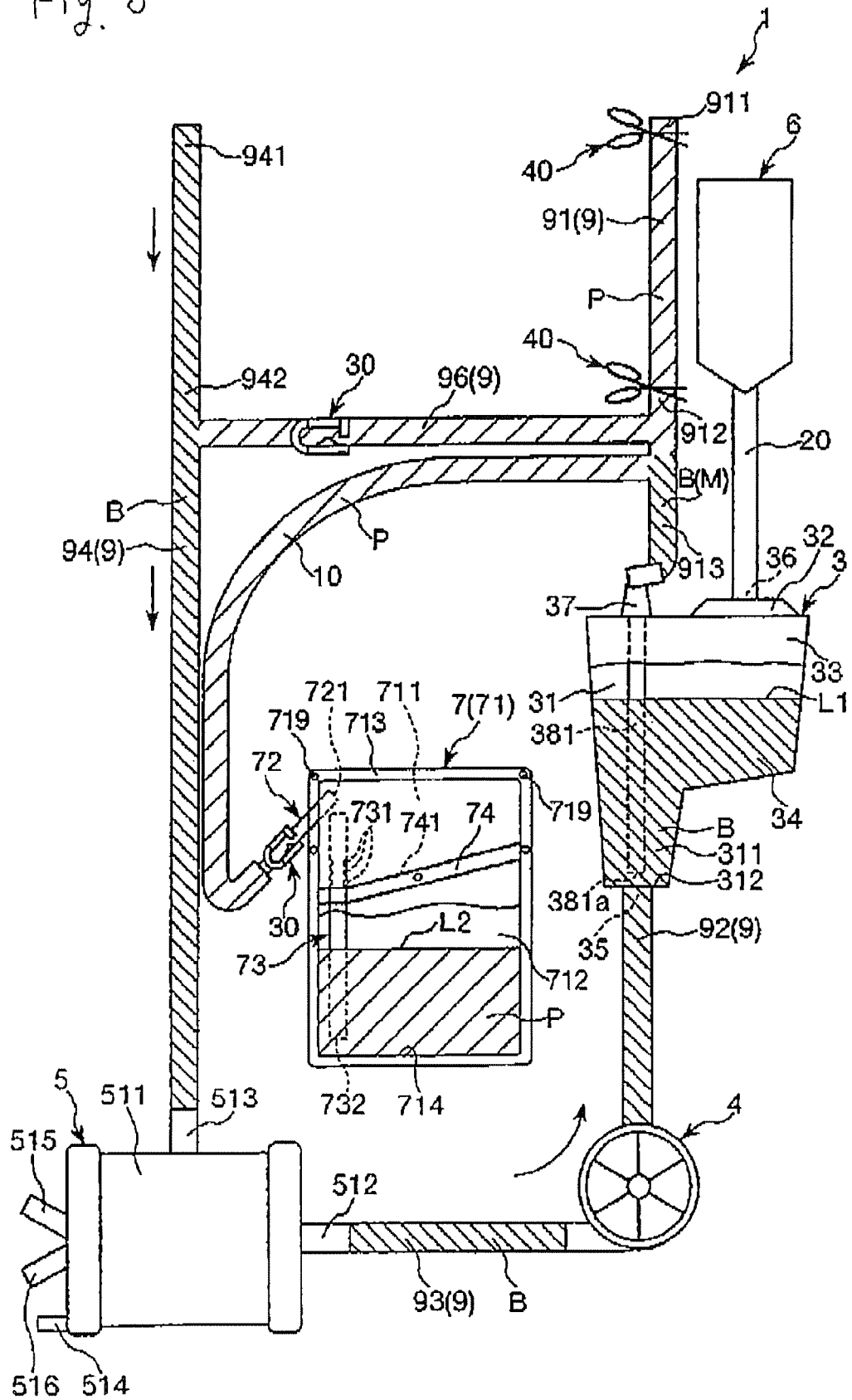
FIG. 8 is a schematic illustration of the circuitry of the extracorporeal circuit illustrated in FIG. 1 showing a further aspect of the manner of use of the disclosed extracorporeal circuit.

After the inflow of the priming solution P is thus stopped, the clamp 30 set to the inlet tube 72 of the collection bag 7 is rendered in a closed state again as indicated in FIG. 8. Further, thereafter, the forceps 40 are removed from the forceps-attached part 942 of the tube 94.

In this state, the blood B flows again in the direction of the arrow in FIG. 8 from the patient via the arterial-line catheter due to the blood pressure and the difference in height. As a result, in the extracorporeal circuit 1, the tube 94, the oxygenator 5, the tube 93, the pump 4, the tube 92, and the blood reservoir 3 are filled with (replaced with) the blood B as indicated in FIG. 8).

After the blood reservoir 3 is filled with a prescribed amount of the blood B, the forceps 40 are set again at the forceps-attached part 942 of the tube 94. As a result, the inflow of the blood B into the tube 94 is stopped. Whereas, the forceps 40 are also set to the forceps-attached part 913 of the tube 91. Thereafter, the tube 91 is connected to a venous-line catheter previously indwelled in the patient.

Figure 9:
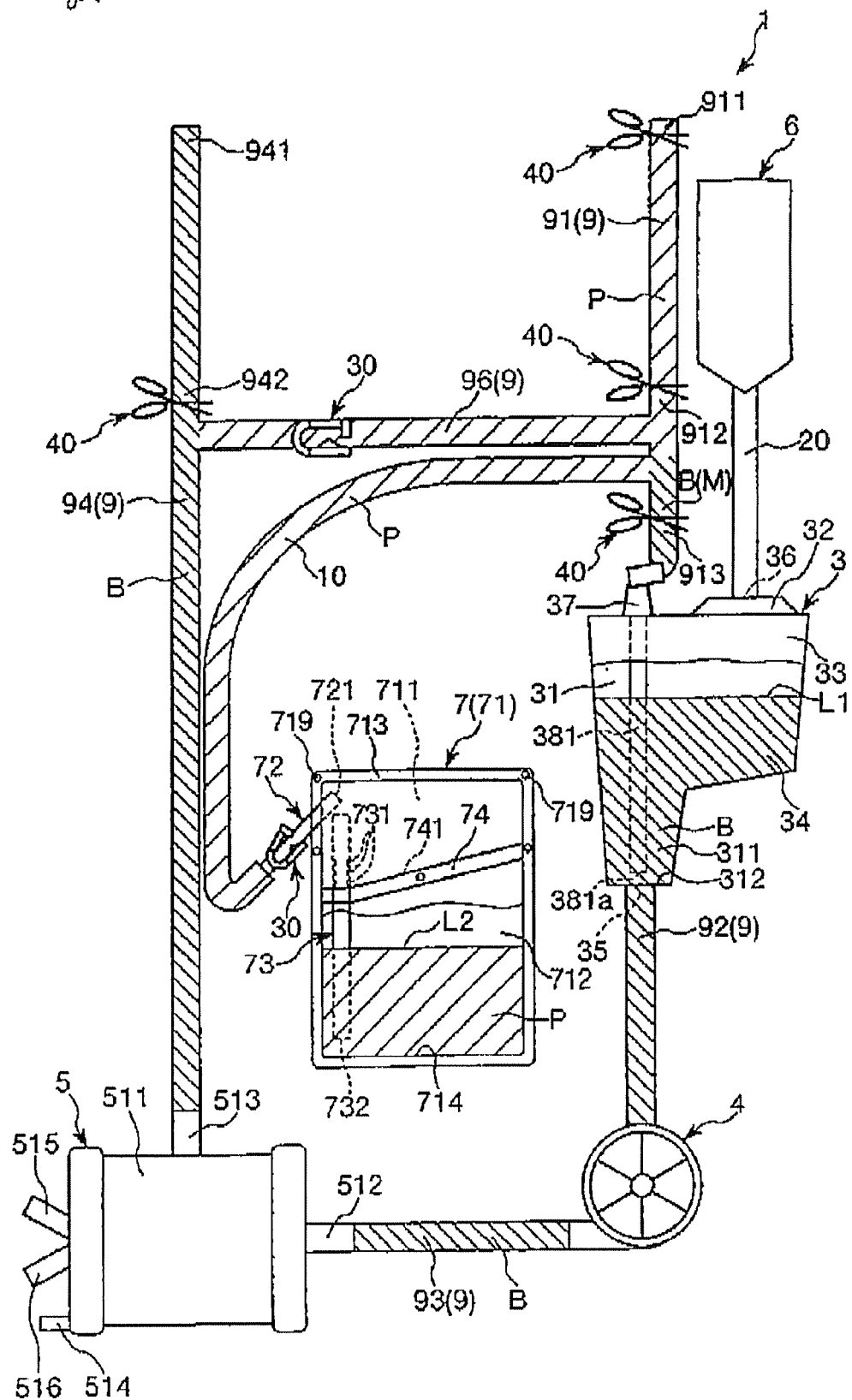
FIG. 9 is a schematic illustration of the circuitry of the extracorporeal circuit illustrated in FIG. 1 showing a further aspect of the manner of use of the disclosed extracorporeal circuit.
Figure 10:
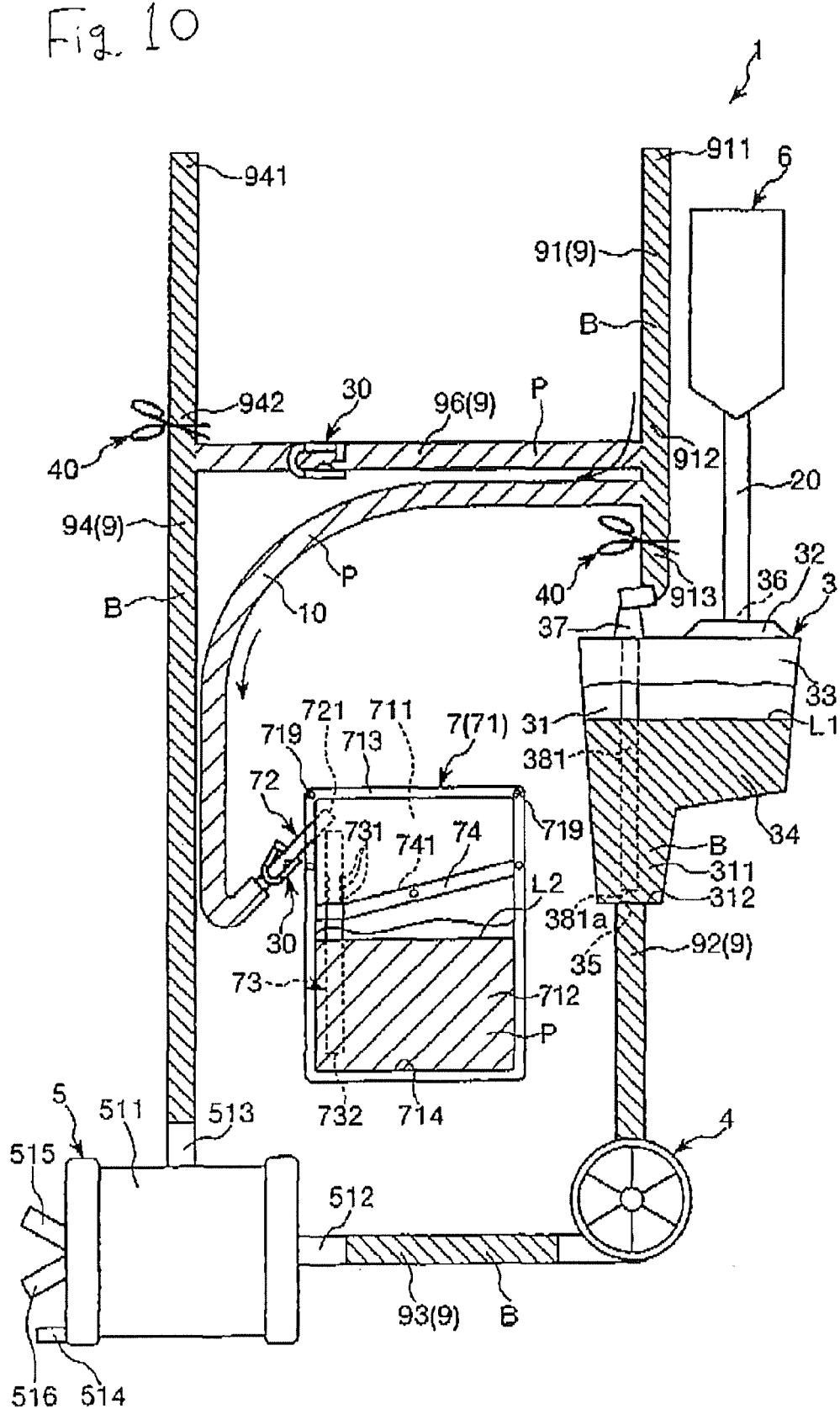
FIG. 10 is a schematic illustration of the circuitry of the extracorporeal circuit illustrated in FIG. 1 showing a further aspect of the manner of use of the disclosed extracorporeal circuit.

In this state, the clamp 30 set to the inlet tube 72 of the collection bag 7 is rendered in an open state again as shown in FIG. 9.

From the state shown in FIG. 9, the forceps 40 set to the forceps-attached parts 911 and 912 of the tube 91 are respectively removed. At this time, the blood B flows from the patient into the tube 91 via the venous-line catheter due to the blood pressure and the difference in height. The blood B which has flowed into the tube 91 thrusts the priming solution P in the tube 91 in the direction of the arrow in FIG. 10. As a result, the priming solution P in the tube 91 is collected via the tube 10 into the collection bag 7.

After the priming solution P in the tube 91 is replaced with the blood B, the clamp 30 set to the inlet tube 72 of the collection bag 7 is rendered in a closed state again. Thereafter, the forceps 40 set to the forceps-attached part 913 of the tube 91 and the forceps 40 set to the forceps-attached part 942 of the tube 94 are respectively removed.

In this state, the blood B flows in the direction of the arrow in FIG. 11 due to the difference in height and the blood pressure. Further, at this step, the pump 4 is operated again.

In other words, when the pump 4 is operated, the blood B drawn via the venous-line catheter from the patient passes through the tube 91 (venous line), and first, flows into the blood reservoir 3. In the blood reservoir 3, bubbles in the blood B are removed by the action of the filter member 382. The blood B from which bubbles have been removed flows out of the connecting port 35 of the blood reservoir 3, passes in the pump 4, and is fed to the oxygenator 5. In the oxygenator 5, gas exchange is carried out on the blood B. The blood B subjected to gas exchange passes through the tube 94 (arterial line), and is returned to the patient via the catheter.

With the foregoing operation, to replace the priming solution P in the extracorporeal circuit 1 with the blood B after the extracorporeal circuit 1 is primed, the clamp 30 set to the tube 10 is operated. With such a relatively simple operation or the like, the priming solution P can be readily and quickly collected in the proper quantity. For this reason, the process can quickly proceeds to the extracorporeal circulation operation using the extracorporeal circuit 1.

Further, the extracorporeal circuit 1 can thrust the priming solution P toward the collection bag 7 by the blood B, i.e., can perform RAP. This can inhibit or prevent the blood B in the extracorporeal circuit 1 from being diluted with the priming solution P.

From the state shown in FIG. 11, the one pair of forceps 40 is set to the forceps-attached part 912 of the tube 91 and another pair of forceps 40 is set to the forceps-attached part 942 of the tube 94. Then, the clamp 30 of the tube 96 can be rendered in an open state (i.e., opened). In this case, the blood B which has come out of the oxygenator 5 passes through the tube 96 (recirculation line) and the blood reservoir 3, and returns to the pump 4 again. Thus, the blood B repeatedly circulates through the annular passage including the pump 4 and the oxygenator 5.

Figure 15:
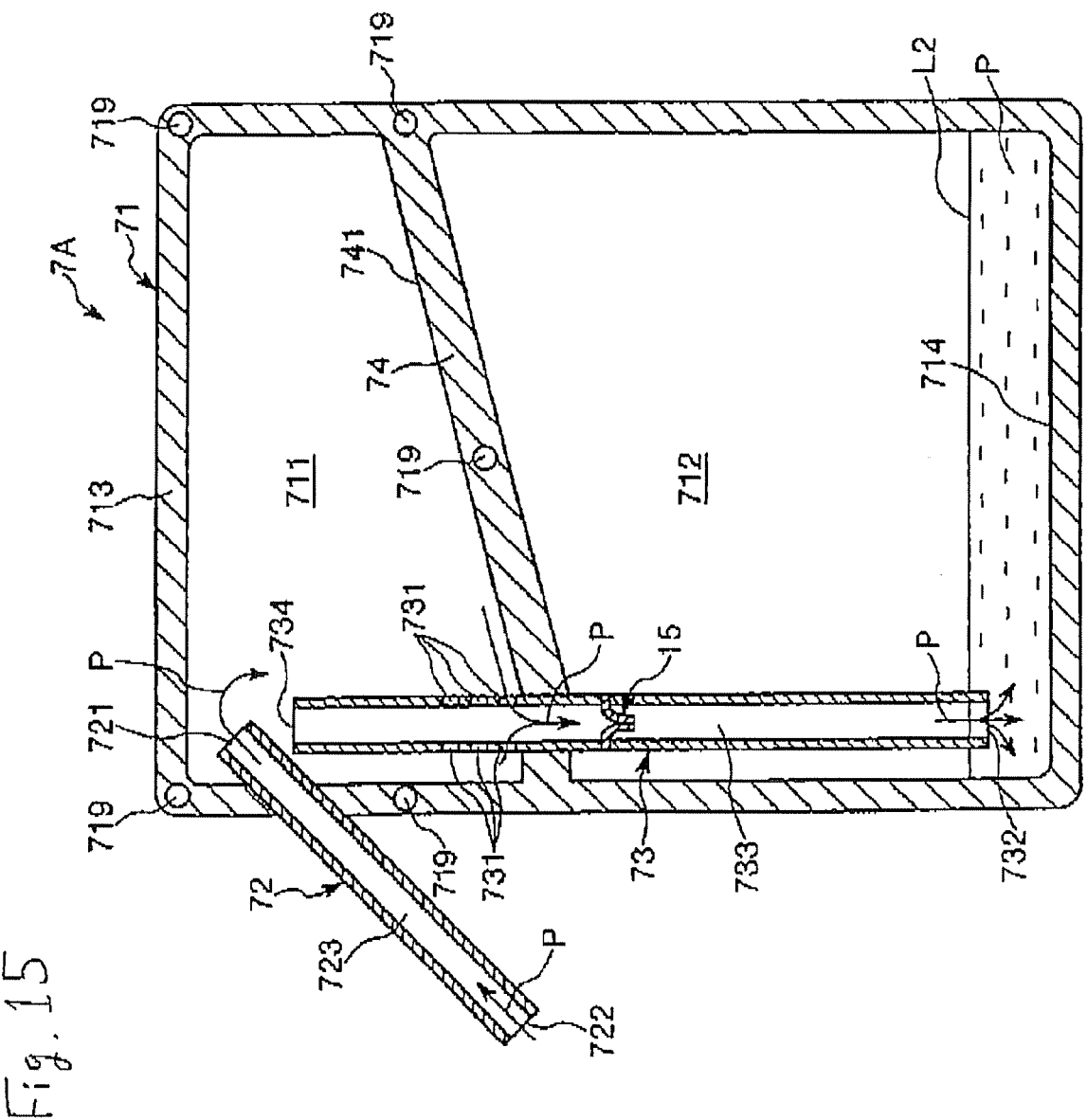
FIG. 15 is a longitudinal cross-sectional view of a second embodiment of a liquid collection bag included in the extracorporeal circuit shown in FIG. 1.

FIG. 15 illustrates a liquid collection bag according to a second embodiment. The following description will focus primarily on differences between this second embodiment of the liquid collection bag and its use in the extracorporeal circuit, and the first embodiment described above. Features associated with the second embodiment of the liquid collection bag that are the same as those previously described are identified by the same reference numerals and a detailed description of such features is not repeated here.

This second embodiment of the collection bag is similar to the first embodiment except that the configurations of the communication parts are different.

The collection bag 7A shown in FIG. 15 includes a check valve 75 is positioned at an intermediate portion (e.g., the middle) of the communication tube 73A. The check valve is positioned between the side hole 731 and the opening 732. The check valve 75 is formed of, for example, a duckbill valve. The check valve 75 can permit flow of a fluid (priming solution P or air) from the first space 711 to the second space 712 in the communication tube 73A, and can forbid or prevent flow in the opposite direction.

Even when the check valve 75 changes the pressure of the inside of the second space 712, the first space 711 is more reliably prevented from receiving the effect of the pressure change. Accordingly, the internal pressure of the first space 711 does not substantially change and so the priming solution P can be collected in the proper quantity.

Figure 16:
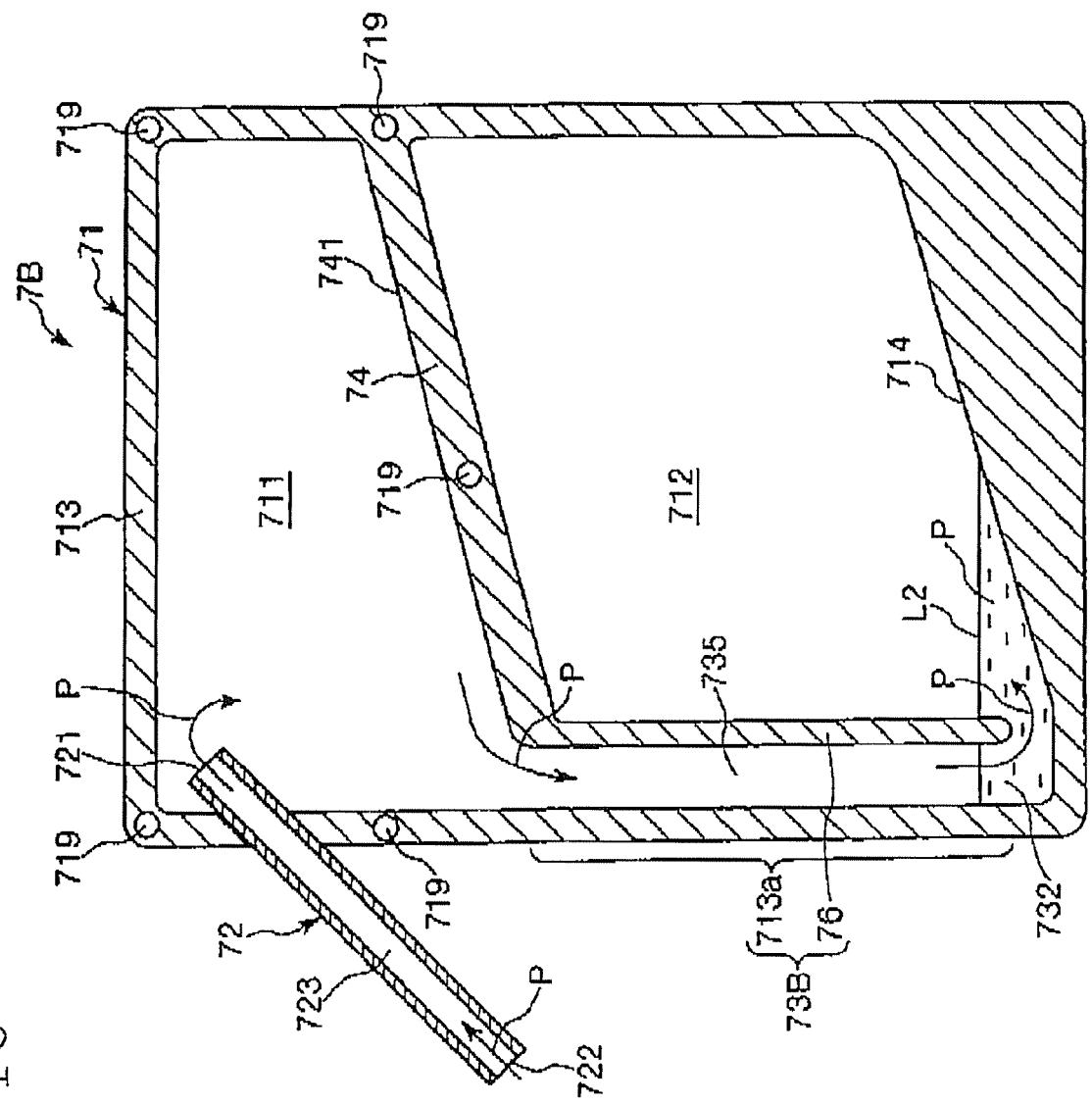
FIG. 16 is a longitudinal cross-sectional view of a third embodiment of a liquid collection bag included in the extracorporeal circuit shown in FIG. 1.

FIG. 16 illustrates a liquid collection bag according to a third embodiment. The following description will focus primarily on differences between this third embodiment of the liquid collection bag and its use in the extracorporeal circuit, and the embodiments described above. Features associated with the third embodiment of the liquid collection bag that are the same as those previously described are identified by the same reference numerals and a detailed description of such features is not repeated here.

This third embodiment is similar to the first embodiment except that the configurations of the bag body and the communication parts are different.

The bag body 71 of the collection bag 7B shown in FIG. 16 includes a fused part 76 continuously formed from one end of the partition part 74. That is, like the partition plate 74, the part 76 can be formed by fusing together the two bag-forming sheets along a region corresponding to the part 76. The fused part 76 extends downwardly in a band and generally forms a wall. The fused part 76 faces a part of the fused part 713 (this part is hereinafter referred to as a "communication part forming part 713a") with a gap 735 interposed therebetween. Thus, the wall 76 is spaced from the fused peripheral edges of the sheets forming the collection bag. With this configuration of the collection bag 7B, the fused part 76 and the communication part forming part 713a function as a communication part 73B for establishing communication between the first space 711 and the second space 712. The gap 735 of the communication part 73B functions as the passage for the priming solution P. When such a communication part 73B is formed in the bag body 71, it can be formed in the same manner as with the fused part 13 and the partition part 74 (in one step). This facilitates manufacturing of the collection bag 7B.

The bottom 714 of the bag body 71 is inclined toward the lower end opening 732 of the communication part 73B. This facilitates the storage of the priming solution P in the vicinity of the lower end opening 732. As a result, in a relatively earlier period from start of flow of the priming solution P into the second space 712, the height of the liquid level L2 of the priming solution P in the second space 712 exceeds the height of the lower end opening 732 of the communication tube 73 as shown in FIG. 16. In this state illustrated in FIG. 16, as with the first embodiment, communication between the part of the second space 712 except for the priming solution P and the first space 711 is blocked by the priming solution P in the second space 712. As a result, even when the pressure of the part of the second space 712 except for the priming solution P changes, the first space 711 is inhibited or prevented from receiving the effect of the pressure change. Accordingly, the internal pressure of the first space 711 does not substantially change. This helps enable the priming solution P to be collected in the proper quantity.

Figure 17:
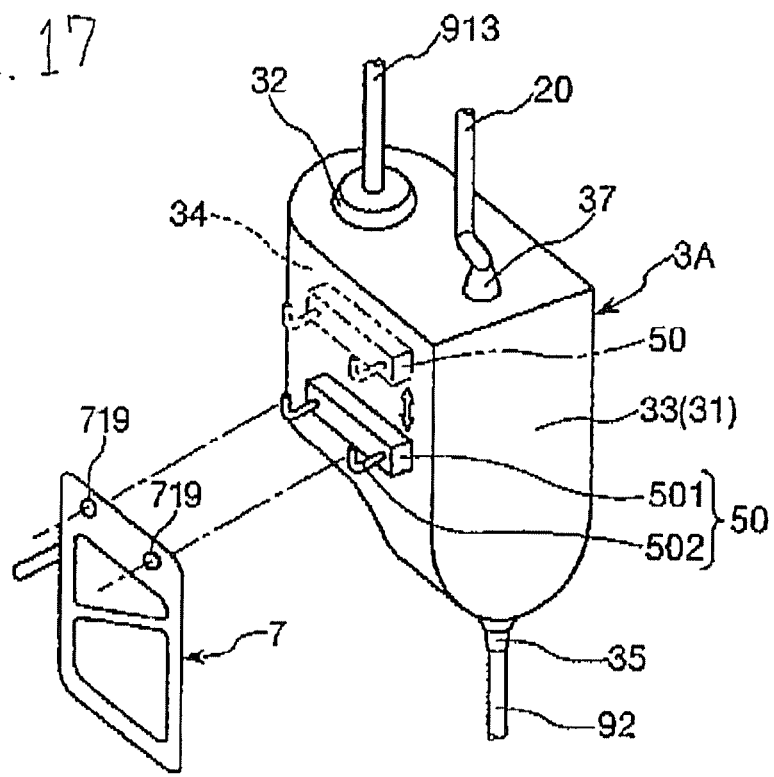
FIG. 17 is a perspective view of a blood reservoir and a collection bag included in an extracorporeal circuit according to a fourth embodiment.

FIG. 17 illustrates a liquid collection bag according to a fourth embodiment. The following description will focus primarily on differences between this fourth embodiment of the liquid collection bag and its use in the extracorporeal circuit, and the embodiments described above. Features associated with the fourth embodiment of the liquid collection bag that are the same as those previously described are identified by the same reference numerals and a detailed description of such features is not repeated here.

This embodiment is similar to the first embodiment except that the configuration of the blood reservoir is different. A holding member 50 for holding (hanging) the collection bag 7 is set on the side surface of the blood reservoir 3A (housing 33) shown in FIG. 17. The holding member 50 includes a plate-like support plate 501 and two hooks 502 supported on and extending from the front side of the support plate 501.

The support plate 501 is formed of the same material as, for example, the material used to fabricate the housing body 31 of the blood reservoir 3A. A double-sided adhesive tape is bonded to the back side of the support plate 501. Attachment of the double-sided adhesive tape enables the holding member 50 to be attached to or detached from the blood reservoir 3A. Accordingly, the setting height of the holding member 50 with respect to the blood reservoir 3A can be changed as indicated by the two-dot chain line in FIG. 17.

Each hook 502 is l-shaped and is formed of a metal material such as stainless steel. By inserting respective hooks 502 into the suspending parts 719 of the collection bag 7, respectively, the collection bag 7 can be used in a suspended (hung) state.

The adhesive strength of the double-sided adhesive tape is set to such a degree that the holding member 50 does not detach from the housing body 31 even when the collection bag 7 is filled with the priming solution P with the collection bag 7 suspended on the holding member 50.

Thus, with the extracorporeal circuit 1 of this embodiment, the holding member 50 is configured such that the setting height of the blood reservoir 3A of the collection bag 7 with respect to the housing body 31 is adjustable. As a result, the amount of the priming solution P to be collected into the collection bag 7 can be appropriately set.

Figure 18:
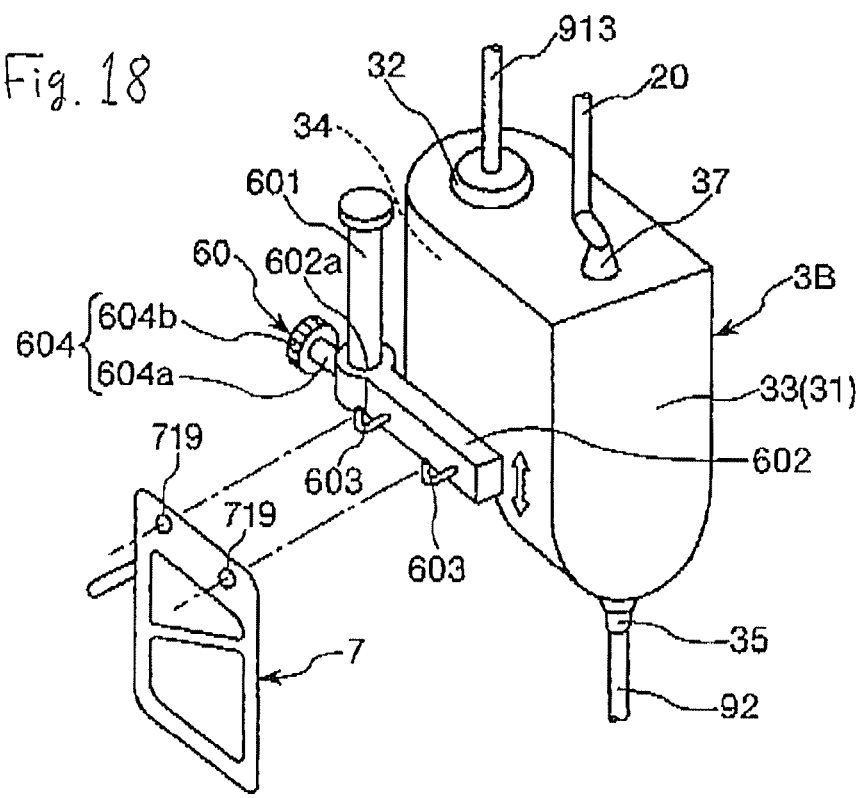
FIG. 18 is a perspective view of a blood reservoir and a collection bag included in an extracorporeal circuit according to a fifth embodiment.

FIG. 18 illustrates a liquid collection bag according to a fifth embodiment. The following description will focus primarily on differences between this fifth embodiment of the liquid collection bag and its use in the extracorporeal circuit, and the embodiments described above. Features associated with the fifth embodiment of the liquid collection bag that are the same as those previously described are identified by the same reference numerals and a detailed description of such features is not repeated here.

This fifth embodiment is similar to the fourth embodiment except that the configuration of the blood reservoir is different. Here, a holding mechanism 60 for holding (hanging) the collection bag 7 is set on the side surface of the blood reservoir 3B (housing 33) shown in FIG. 18. The holding mechanism 60 includes a column 601 supported at its lower end by the housing body 31 of the blood reservoir 3B (i.e., the lower end of the column 601 is fixed to the housing body 31), a moving member 602 positioned on the column 601 and movable along the longitudinal extent of the column 601, two hooks 603 supported by and extending outwardly from the moving member 602, and a setscrew (fixing member) 604 for fixing the moving member 602 to the column 601.

The column 601 has a cylindrical outer shape. The moving member 602 is an elongated member and has a hole 602a at one end portion receiving the column 601. A threaded hole is provided at the side part of the moving member 602. This through hole communicates with the hole 602a.

Each hook 603 is L-shaped and is formed of a metal material such as stainless steel. Further, these hooks 603 are spaced apart from each other in the longitudinal direction of the moving member 602. By inserting respective hooks 603 in their corresponding suspending parts 719 of the collection bag 7, the collection bag 7 can be used in a suspended state.

The setscrew 604 includes a male screw part 604a, and a head part 604b at one end of the male screw part 604a. The male screw part 604 of the setscrew 604 is screwed into the threaded through hole of the moving member 602. Further, the other end of the female screw part 604 is engaged with the outer circumferential surface of the column 601. As a result, the moving member 602 can be fixed to the column 601, and hence the collection bag 7 can be held at a prescribed position (height).

By loosening the setscrew 604, the fixing of the moving member 602 is released. Thus, the moving member 602 can be moved. As a result, the setting height of the collection bag 7 with respect to the blood reservoir 3B can be changed.

Thus, with the extracorporeal circuit 1 of this embodiment, the setting height of the collection bag 7 with respect to the blood reservoir 3A can be adjusted by movement of the moving member 602 of the holding mechanism 60. As a result, the amount of the priming solution P to be collected in the collection bag 7 can be appropriately set.

The column 601 has a cylindrical outer shape. As a result, once the setscrew 604 is operated to release the moving member 602, the moving member 602 can be rotated about the shaft of the column 601. The orientation of the held collection bag 7 can thus be changed according to, for example, the standing position of a user. As a result of this, the collection state of the priming solution P to be collected in the collection bag 7 can be visually observed with relative ease.

Figure 19:
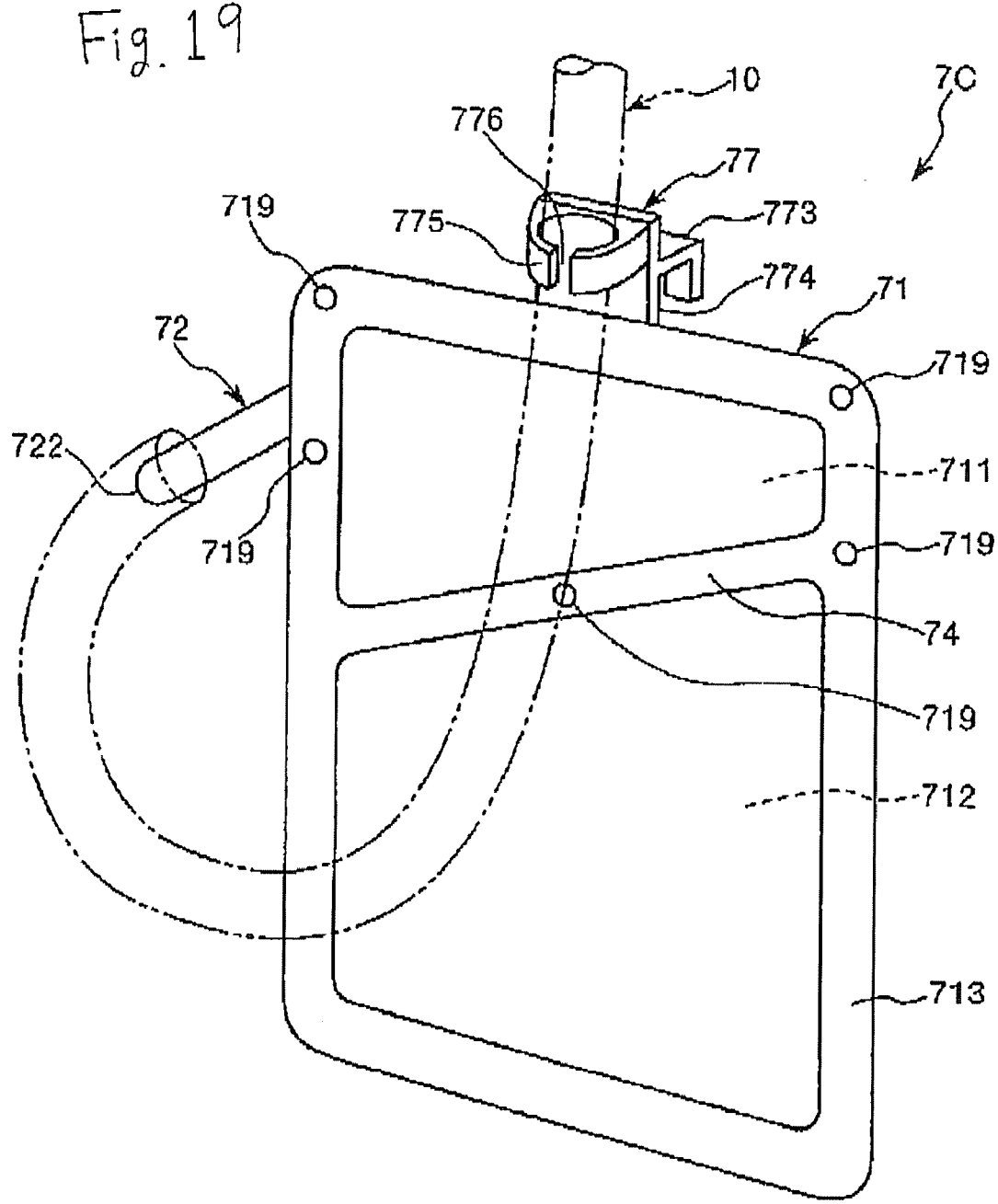
FIG. 19 is a front perspective view of a collection bag to be used in an extracorporeal circuit according to a sixth embodiment.
Figure 20:
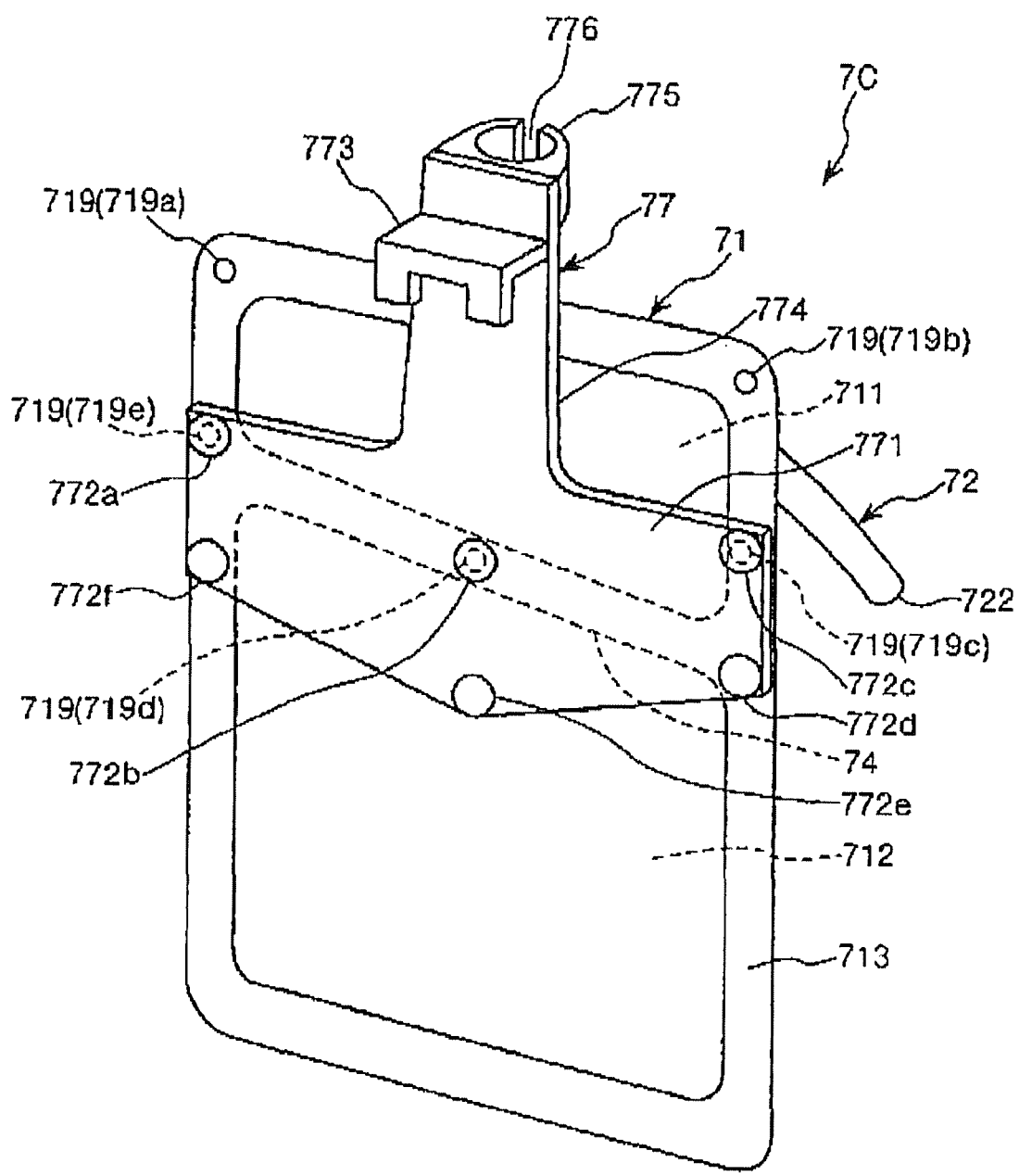
FIG. 20 is a back perspective view of the collection bag according to the sixth embodiment.

FIGS. 19 and 20 illustrate a liquid collection bag according to a further embodiment. The following description will focus primarily on differences between this sixth embodiment of the liquid collection bag and its use in the extracorporeal circuit, and the embodiments described above. Features associated with the sixth embodiment of the liquid collection bag that are the same as those previously described are identified by the same reference numerals and a detailed description of such features is not repeated here.

This embodiment is similar to the first embodiment except that the configuration of the suspending part of the collection bag is different. The collection bag 7C shown in FIGS. 19 and 20 has a detachable suspending instrument (suspending part) 77. The suspending instrument 77 has an elongated support plate 771, six buttons 772a, 772b, 772c, 772d, 772e, 772f supported by the support plate 771, a hook part 773, and a connecting part 774 for connecting the hook part 773 and the support plate 771.

The support plate 771 is a plate member having almost the same length as the width of the bag body 71. The support plate 771 supports the buttons 772a-772f.

Respective buttons 772a-772f are fittable into prescribed suspending parts 719 of the bag body 71. By fitting respective buttons 772a-772f into prescribed suspending parts 719, the suspending instrument 77 can be mounted to the bag body 71. By releasing the respective fits, the suspending instrument 77 can be removed (detached) from the bag body 71. As a result, it is possible to select whether the suspending instrument 77 is used, or is not used.

The hook part 773 is positioned above the support plate 771. The hook part 773 is L-shaped in side view, and is a site capable of engaging (i.e., being hooked on), for example, the moving member 83 of the collection bag support device 8 or the moving member 602 of the holding mechanism 60. As a result, the collection bag 7C with the suspending instrument 77 mounted therein (in the state (mounted state) shown in FIGS. 19 and 20) can be suspended on the collection bag support device 8 or the holding mechanism 60.

The side of the collection bag 7C opposite from the hook part 773 (i.e., the front side of the collection bag 7C) is provided with a tube holding part 775 for holding the tube 10. The tube holding part 775 is generally in the form of a ring, and has a notch part (cut-out) 776 obtained by cutting off a part of the tube holding part 775. The tube-holding part 775 is thus C-shaped. Attachment or detachment of the tube 10 with respect to the tube holding part 775 can thus be performed.

Further as described above, on the support plate 771, the buttons 772a-772f are supported. For convenience of description, five suspending parts 719 of the bag body 71 are referred to as the "suspending parts 719a, 719b, 719c, 719d, 719e" sequentially clockwise from the suspending part 719 at upper left of FIG. 20. With the suspending instrument 77 in the configuration and orientation shown in FIG. 20, the button 772a fits to the suspending part 719e of the bag body 71; the button 772b fits to the suspending part 719d of the bag body 71; and the button 772c fits to the suspending part 719c of the bag body 71. The way in which the suspending instrument 77 is mounted is not limited to the way of mounting shown in FIG. 20.

In addition, the button 772f can fit to the suspending part 719e of the bag body 71; the button 772e can fit to the suspending part 719d of the bag body 71; and the button 772d can fit to the suspending part 719c of the bag body 71. As a result, the mounting position of the suspending instrument 77 with respect to the bag body 71 can be changed. Therefore, the setting height of the collection bag 7C with respect to the blood reservoir 3 can be adjusted. The amount of priming solution P to be collected in the collection bag 7C can be appropriately set according to the circumstances or situation.

The materials for forming the suspending part 77 are not particularly restricted. However, for example, various metal materials and various resin materials can be used.

The liquid collection bag and the extracorporeal circuit have been described by way of several illustrated embodiments. However, the present invention is not limited in this regard. Respective parts forming the liquid collection bag and the extracorporeal circuit can be replaced with the parts capable of exerting the same or similar effects. Further, components beyond those described above may be added.

Also, the liquid collection bag and the extracorporeal circuit disclosed here may be a combination of two or more aspects (features) of the respective embodiments.

The description above describes the use of clamps to open and close various tubes forming the extracorporeal circuit. However, the invention is not limited thereto. For example, a valve is also acceptable.

The principles, embodiments and modes of operation of the liquid collection bag and extracorporeal circuit have been described in the foregoing specification, but the invention which is intended to be protected is not to be construed as limited to the particular embodiments disclosed. The embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. A method of priming a circuit to be used in extracorporeal blood circulation, the method comprising:
    connecting a blood reservoir of the circuit to a source of priming solution that is not blood, the blood reservoir possessing a bottom, the circuit comprising: an oxygenator, an arterial line connected to the oxygenator, a pump, a first line connecting in a fluid communicating manner the pump and the bottom of the blood reservoir, a second line connecting in a fluid communicating manner the pump and the oxygenator, a venous line connected to the blood reservoir, a flexible collection container possessing an interior, and a third line branching from the venous line and having an open end opening into the interior of the collection container;
    positioning the collection container so that the open end of the third line is positioned elevationally below an objective height in the blood reservoir;
    introducing the priming solution that is not blood into the blood reservoir from the source while the third line is closed, the priming solution flowing from the blood reservoir through the first line, through the pump, through the second line, through the oxygenator and through the arterial line; and
    opening the third line after the priming solution in the blood reservoir is elevationally at or above the objective height so that the priming solution automatically flows into the collection container.

2. A method according to claim 1, further comprising closing the third line after the priming solution in the blood reservoir is lowered to the objective height and while priming solution remains in the blood reservoir, and thereafter connecting the arterial line to an artery of a patient and connecting the venous line to a vein of a patient so that blood flows from the patient toward the blood reservoir in a direction opposite a direction of flow of the priming solution.

3. A method according to claim 2, wherein the flow of the blood from the patient toward the blood reservoir in the direction opposite the direction of flow of the priming solution causes the priming solution in the oxygenator, the arterial line, the pump, the first line and the second line to be replaced by the blood from the patient.

4. A method according to claim 2, wherein the flow of the blood from the patient toward the blood reservoir causes the blood to enter the blood reservoir and mix with at least some of the priming solution remaining in the blood reservoir, and further comprising re-opening the third line after the blood from the patient has entered the blood reservoir and mixed with at least some of the remaining priming solution in the blood reservoir to produce a blood/priming solution mixture such that a level of liquid in the blood reservoir is above the objective height.

5. A method according to claim 4, wherein the re-opening of the third line when the level of the liquid in the blood reservoir is above the objective height causes at least some of the priming solution in the blood reservoir which has not mixed with the blood and at least some of the blood/priming solution mixture to flow into the collection container.

6. A method according to claim 1, wherein an interior of the collection container is partitioned by a partition into a first space positioned vertically above a second space, and wherein the priming solution automatically flows into the first space of the collection container, the priming solution in the first space of the collection container flowing into the second space by way of a communication part, the communication part having an open end in the second space positioned adjacent to and facing a bottom wall of the collection container.

7. A method of priming a circuit to be used in extracorporeal blood circulation, the method comprising:
    connecting a blood reservoir of the circuit to a source of priming solution, the blood reservoir possessing a bottom, the circuit comprising: an oxygenator, an arterial line connected to the oxygenator, a pump, a first line having one end connected to the pump and an other end connected to the bottom of the blood reservoir to connect the pump and the blood reservoir to one another in a fluid communicating manner, a second line having one end connected to the pump and an opposite end connected to the oxygenator to connect the pump and the oxygenator to one another in a fluid communicating manner, a venous line connected to the blood reservoir, a flexible collection container possessing an interior, and a third line having one end connected to the venous line at a position spaced from the blood reservoir so that the third line and the venous line fluidly communicate with one another and an opposite end which is open into the interior of the collection container;

positioning the collection container so that the open second end of the third line is positioned elevationally below an objective height inside the blood reservoir;

introducing the priming solution into the blood reservoir from the source before introducing any blood into the blood reservoir and while the third line is closed, the priming solution flowing from the blood reservoir through the first line, through the pump, through the second line, through the oxygenator and through the arterial line; and opening the third line after the priming solution in the blood reservoir is elevationally at or above the objective height so that the priming solution automatically flows into the interior of the collection container by way of the third line.

8. A method according to claim 7, wherein the priming solution flows from the source through the circuit in a priming solution flow direction, further comprising closing the third line after the priming solution in the blood reservoir is lowered to the objective height and while priming solution remains in the blood reservoir, and thereafter connecting the arterial line to an artery of a patient and connecting the venous line to a vein of a patient so that blood flows from the patient toward the blood reservoir in a direction opposite the priming solution flow direction.

9. A method according to claim 8, wherein the flow of the blood from the patient toward the blood reservoir in the direction opposite the priming solution flow direction replaces the priming solution in the oxygenator, the arterial line, the pump, the first line and the second line with the blood from the patient.

10. A method according to claim 8, wherein the blood flowing from the patient toward the blood reservoir enters the blood reservoir and mixes with at least some of the priming solution remaining in the blood reservoir, and further comprising re-opening the third line after the blood from the patient enters the blood reservoir and mixes with at least some of the remaining priming solution in the blood reservoir to produce a blood/priming solution mixture such that a level of liquid in the blood reservoir is above the objective height.

11. A method according to claim 10, wherein the re-opening of the third line when the level of the liquid in the blood reservoir is above the objective height causes at least some of the priming solution in the blood reservoir which has not mixed with the blood and at least some of the blood/priming solution mixture to flow into the collection container.

12. A method according to claim 7, wherein the interior of the collection container is partitioned by a partition into a first space positioned vertically above a second space, and wherein the priming solution automatically flows into the first space of the collection container by way of the third line, the priming solution in the first space of the collection container flowing into the second space by way of a communication part, the communication part having an open end in the second space positioned adjacent to and facing a bottom wall of the collection container.

13. A method according to claim 7, wherein the priming solution flows in a priming solution flow direction from the source to the blood reservoir and then through the first line, then through the pump, then through the second line, then through the oxygenator and then through the arterial line, and thereafter connecting the arterial line to an artery of a patient and connecting the venous line to a vein of a patient so that blood flows from the artery of the patient into the arterial line toward the blood reservoir in a direction opposite the priming solution flow direction.

14. A method according to claim 7, wherein the interior of the collection container includes a first space positioned vertically above a second space, and wherein after the opening of the third line the priming solution automatically flows into the first space of the interior of the collection container before entering the second space.

15. A method of priming a circuit to be used in extracorporeal blood circulation, the method comprising:

connecting a blood reservoir of the circuit to a source of priming solution, the blood reservoir possessing a bottom, the circuit comprising: an oxygenator, an arterial line connected to the oxygenator, a pump, a first line connecting in a fluid communicating manner the pump and the bottom of the blood reservoir, a second line connecting in a fluid communicating manner the pump and the oxygenator, a venous line connected to the blood reservoir, a flexible collection container possessing an interior, and a third line having a first end opening into the venous line at a position spaced from the blood reservoir and having an oppositely located open second end positioned in the interior of the collection container;

positioning the collection container so that the open second end of the third line is positioned elevationally below an objective height inside the blood reservoir;

introducing the priming solution into the blood reservoir from the source before introducing any blood into the blood reservoir and while the third line is closed, the priming solution flowing from the blood reservoir into the first line, from the first line into the pump, from the pump into the second line, from the second line into the oxygenator, and from the oxygenator into the arterial line, and wherein the priming solution does not enter the collection container while the third line is closed; and opening the third line after the priming solution in the blood reservoir is elevationally at or above the objective height so that the priming solution automatically flows into the collection container by way of the third line.

16. A method according to claim 15, wherein the priming solution flows through the circuit in a priming solution flow direction from the source to the blood reservoir, then through the first line, then through the pump, then through the second line, then through the oxygenator and then through the arterial line, and thereafter connecting the arterial line to an artery of a patient and connecting the venous line to a vein of a patient so that blood flows from the artery of the patient into the arterial line toward the blood reservoir in a direction opposite the priming solution flow direction.

17. A method according to claim 16, wherein the flow of the blood from the patient toward the blood reservoir in the direction opposite the priming solution flow direction replaces the priming solution in the oxygenator, the arterial line, the pump, the first line and the second line with the blood from the patient.

18. A method according to claim 16, wherein the blood flowing from the patient toward the blood reservoir enters the blood reservoir and mixes with at least some of the priming solution remaining in the blood reservoir, and further comprising re-opening the third line after the blood from the patient enters the blood reservoir and mixes with at least some of the remaining priming solution in the blood reservoir to produce a blood/priming solution mixture such that a level of liquid in the blood reservoir is above the objective height.

19. A method according to claim 18, wherein the re-opening of the third line when the level of the liquid in the blood reservoir is above the objective height causes at least some of the priming solution in the blood reservoir which has not mixed with the blood and at least some of the blood/priming solution mixture to flow into the collection container.

20. A method according to claim 15, wherein the interior of the collection container includes a first space positioned vertically above a second space, and wherein the priming solution automatically flows into the first space of the interior of the collection container before flowing into the second space.

* * * * *